(12) United States Patent
Owens et al.

(10) Patent No.: US 7,202,348 B2
(45) Date of Patent: Apr. 10, 2007

(54) MONOCLONAL ANTIBODY ANTAGONISTS FOR TREATING MEDICAL PROBLEMS ASSOCIATED WITH D-AMPHETAMINE-LIKE DRUGS

(75) Inventors: Samuel M. Owens, Little Rock, AR (US); Frank Ivy Carroll, Durham, NC (US); Philip Abraham, Cary, NC (US)

(73) Assignee: The University of Arkansas for Medical Sciences, Little Rock, AR (US)

( * ) Notice: Subject to any disclaimer, the term of this patent is extended or adjusted under 35 U.S.C. 154(b) by 464 days.

(21) Appl. No.: 10/255,462

(22) Filed: Sep. 26, 2002

(65) Prior Publication Data

US 2003/0119083 A1 Jun. 26, 2003

Related U.S. Application Data

(63) Continuation-in-part of application No. 09/839,549, filed on Apr. 20, 2001, now Pat. No. 6,669,937.

(60) Provisional application No. 60/198,902, filed on Apr. 20, 2000.

(51) Int. Cl.
*C07K 16/44* (2006.01)

(52) U.S. Cl. ................. 530/388.9; 530/389.8

(58) Field of Classification Search ............ 530/388.9, 530/389.8
See application file for complete search history.

(56) References Cited

U.S. PATENT DOCUMENTS

| 4,329,281 | A | * | 5/1982 | Christenson et al. | .... 530/389.8 |
|---|---|---|---|---|---|
| 5,041,076 | A | * | 8/1991 | Kantor | ........................ 494/37 |
| 5,135,863 | A | * | 8/1992 | Hu et al. | ..................... 435/188 |
| 5,238,652 | A | * | 8/1993 | Sun et al. | ...................... 422/61 |
| 5,492,841 | A | * | 2/1996 | Craig | .......................... 436/534 |
| 5,976,812 | A | * | 11/1999 | Huber et al. | ................. 435/7.1 |
| 6,087,184 | A | * | 7/2000 | Magginetti et al. | ......... 436/514 |
| 6,306,616 | B1 | * | 10/2001 | Shindelman | ............... 435/7.93 |

FOREIGN PATENT DOCUMENTS

| EP | 343346 A1 | * | 11/1989 |
|---|---|---|---|
| EP | 574782 A2 | * | 12/1993 |
| WO | WO-92/03163 A1 | * | 3/1992 |
| WO | WO-97/49721 A1 | * | 12/1997 |

* cited by examiner

*Primary Examiner*—Mary E. Ceperley
(74) *Attorney, Agent, or Firm*—Benjamin Aaron Adler

(57) ABSTRACT

The present invention provides synthetic immunochemical haptens for the generation of antibodies that are designed to recognize the common molecular features of d-methamphetamine-like abused stimulants with insignificant cross-reactivity to endogenous substrates (e.g. dopamine) or over-the-counter medications (e.g. l-methamphetamine, pseudoephedrine, phenylpropanolamine and ephedrine). These monoclonal antibodies and their antigen binding fragments are useful in treatment plans for recovering addicts, in emergency room settings for rapidly reversing a drug overdose, in protection of fetuses from drug-abusing pregnant mothers or in a psychiatric setting to reduce the exacerbation of psychotic disorders caused by stimulant drugs.

10 Claims, 26 Drawing Sheets

*d*-Amphetamine (+)Methamphetamine

MDMA

10

X = 2 to 9
connection at 2,
3, or 4 position

11

X = 1 to 6
connection at 2,
3, or 4 position

12

X = 1 to 6
connection at 2,
3, or 4 position

13

X = 2 to 4
Y = 1 to 5
connection at 2,
3, or 4 position

14

X = 2, 3
connection at 2,
3, or 4 position
R = alkyl 1-5 carbon

15
X = 2 to 9
connection at 2,
3, or 4 position

16
X = 1 to 6
connection at 2,
3, or 4 position

17
X = 1 to 6
connection at 2,
3, or 4 position

18
X = 2 to 4
Y = 1 to 5
connection at 2,
3, or 4 position

19
X = 2, 3
connection at 2,
3, or 4 position
R = alkyl 1-5 carbon

20

X = 3 to 8
connection at 2,
3, or 4 position

21

X = 2 to 7
connection at 2,
3, or 4 position

22

X = 2 to 7
connection at 2,
3, or 4 position

23

X = 1 to 6
connection at 2,
3, or 4 position

24

X = 1 to 6
connection at 2,
3, or 4 position (a) (R)-C₆H₅CH(NH₂)CH₃, toluene
(b) Raney Ni/H₂
(c) HCO₂H/Ac₂O
(d) BBr₃
(e) NaH/Br(CH₂)₅CO₂CH₃
(f) BH₃
(g) Pd/HCO₂H
(h) Dilute HCl

MONOCLONAL ANTIBODY ANTAGONISTS FOR TREATING MEDICAL PROBLEMS ASSOCIATED WITH D-AMPHETAMINE-LIKE DRUGS

CROSS-REFERENCE TO RELATED APPLICATION

This is a continuation-in-part application of U.S. Ser. No. 09/839,549 filed Apr. 20, 2001, now U.S. Pat. No. 6,669,937 which claims benefit of provisional patent application 60/198,902, filed Apr. 20, 2000, now abandoned.

FEDERAL FUNDING LEGEND

This invention was produced in part using funds obtained through grant number R01 DA11560 from the National Institutes of Health. Consequently, the federal government has certain rights in this invention.

BACKGROUND OF THE INVENTION

1. Field of the Invention

The present invention relates generally to the field of drug abuse and addiction therapy. More specifically, the present invention relates to the generation and use of high affinity monoclonal antibodies (MAb) and their derivatives as long acting stimulant antagonists for treating medical problems associated with drug abuse and addiction. In addition, the antigen binding fragments (Fab) and other small molecular fragments of these monoclonal antibodies can serve as a shorter acting stimulant antagonist for treating medical problems like drug overdose.

2. Description of the Related Art

Knowledge gained from basic research into the neurobiology of drug abuse has led to major discoveries in medicine. Nevertheless, the development of medical strategies for treating the complex array of neurological problems associated with drug abuse has been frustratingly slow. In particular, development of medical treatments for alleviating the adverse psychosocial and health effects of d-methamphetamine and similar stimulants is badly needed.

d-Methamphetamine-related hospital emergency cases across the U.S. increased 256% from 1991 to 1994 (Collings, 1996). Toxic effects due to excessive d-methamphetamine use led to more than 10,000 hospital visits each year between 1994 and 1999 and were responsible for more than 2,000 deaths over those same 5 years (Drug Abuse Warning Network, December 2000). The 1995 Toxic Exposure Surveillance System data showed there were 7,601 people treated in health care facilities for amphetamine-like drugs and other stimulants. This is particularly striking since during the same period there were only 3,440 cases of cocaine treatment and a total of 5,170 cases of all types of legal and illegal narcotics (including morphine, codeine and heroin). The current rise in d-methamphetamine use is also alarming because, unlike cocaine, it does not have to be imported. Even an amateur chemist can synthesize this drug in his home using easily obtained reagents and equipment.

Methamphetamine overdose patients can be hyperactive, agitated, and paranoid; and even one-time use of a high dose can lead to a psychotic state lasting several days or weeks. Other complications include hyperthermia, seizures, hypertension, and cardiotoxicity. Recent studies suggest that signs of neurotoxicity (e.g., decreased dopamine transporter density) are present in chronic d-methamphetamine abusers, and these changes appear to correlate with a decrease in cognitive function.

Because there are no specific pharmacological therapies for d-methamphetamine overdose, patients receive palliative and supportive care for symptoms while waiting for the drug to be eliminated by metabolism and renal excretion. Emergency care of patients includes maintenance of ventilation, hydration, electrolyte balance and control of body temperature. Some physicians also choose to administer medications to treat seizures, agitation, or hypertensive crises. Such treatments can aid in managing patients' symptoms, but they do so without removing the causative agent. It would be advantageous to have a medication that could quickly antagonize d-methamphetamine effects by removing the drug from the central nervous system, thereby reversing many of the acute toxicities and reducing the potential for long-term neurological damage.

One reason why clinically effective d-methamphetamine agonists or antagonists have not been discovered is that d-methamphetamine acts at several sites in the central nervous system through multiple mechanisms of action. These mechanisms include, but are not limited to, disruption of vesicular storage of dopamine, inhibition of monoamine oxidase, increased dopamine and serotonin release, and inhibition of dopamine and serotonin reuptake by their respective transporters. In addition, it is likely that any chemical antagonist (or agonist) would share at least some of the adverse effects of d-methamphetamine (e.g., disruption of neurotransmitter homeostasis).

One biologically based approach to treat drug overdose is the use of high-affinity, drug-specific antibodies or Fab fragments. In addition to being relatively safe, except for occasional allergic reactions that can be prevented by the use of humanized monoclonal antibodies, antibody-based therapies act as pharmacokinetic antagonists which gives them several important advantages over treatment with more conventional receptor antagonists. Firstly, there is no receptor antagonist for d-methamphetamine effects at any of its sites of action in the CNS. One of the limitations of development of receptor antagonists is that they will only be capable of attenuating the effects at one type of receptor. Most drugs of abuse have multiple sites of action. Secondly, unlike conventional receptor antagonists (or agonists), antibodies do not inhibit the actions of normal endogenous ligands. In fact, it could be argued that removal of the drug by antibodies might allow for a more normal recovery than treatment with a chemically-derived small molecule competitive agonist or antagonist. Thirdly, since antibodies (and their derivatives like Fab) have extremely high affinities and do not cross the blood-brain barrier, they actually lower drug concentrations throughout the CNS. This allows for a rapid, neuroprotective effect at all sites of action in the CNS.

While monoclonal antibody (mAb) therapy could be a viable approach for antagonizing d-methamphetamine effects, several factors complicate the design of antibody therapy for this drug. First, knowledge of the relationship between antibody affinity and therapeutic efficacy is limited. Previous studies have shown that a single dose of a high-affinity anti-phencyclidine mAb Fab fragment ($K_d$=1.8 nM) is very effective at reversing a phencyclidine-induced overdose in rats (Valentine et al., 1996; Hardin et al., 1998), and that the intact IgG (Kd=1.3 nM) can produce long-term reductions in brain phencyclidine concentrations (Proksch et al., 2000). While these preclinical data for phencyclidine are impressive, the optimal conditions for achieving such profound effects are not clear. Second, unlike most drugs of abuse, d-methamphetamine (d-METH) has a major active metabolite, d-amphetamine (d-AMP). This metabolite is present at significant concentrations in study rats, and d-AMP area under the concentration-versus-time curves (AUC) constitutes 30% and 26% of the total AUC for d-METH and d-AMP in serum and brain, respectively (Rivière et al., 2000). Thus, pharmacological effects due to d-METH and d-AMP may need to be treated in rats. In humans, however, d-AMP's AUC is <15% of the total serum AUC of d-METH and d-AMP (Cook et al., 1993). Therefore, d-AMP may not contribute as significantly to d-METH's effects in humans.

Thus, the prior art is deficient in the lack of effective means of treating d-methamphetamine overdose and addiction by antibody-based therapy. The present invention fulfills this long-standing need and desire in the art.

SUMMARY OF THE INVENTION

The present invention is drawn to the generation of high affinity monoclonal antibodies, and the use of intact and smaller derivatives of the antibodies for treating the medical problems associated with stimulant drug abuse. D-Methamphetamine is the prototypic amphetamine-like drug molecule since it has severe addiction liability, and repeated use of the drug can lead to life-threatening cardiovascular problems, severe depression, psychosis, violent behavior and significant criminal activity. The antibodies are specifically designed to recognize the unique and/or common molecular features of several dangerous stimulant and hallucinogenic drugs of abuse and their psychoactive metabolites, e.g., d-methamphetamine, d-amphetamine, (+/−) 3,4-methylenedioxymethamphetamine (MDMA), and (+/−) 3,4-methylenedioxyamphetamine (MDA) or structurally related stimulants and/or hallucinogenic analogs.

In one embodiment of the present invention, there are provided monoclonal antibodies or antibody fragments that are specifically designed to recognize the common molecular features of several dangerous stimulant and hallucinogenic drugs of abuse and their psychoactive metabolites. These drugs and metabolites include d-methamphetamine, (+/−) 3,4-methylenedioxymethamphetamine, d-amphetamine, and (+/−) 3,4-methylenedioxyamphetamine or structurally related stimulants or hallucinogenic analogs.

In another embodiment of the present invention, there are provided methods of using these monoclonal antibodies or antibody fragments to treat stimulant drug abuse or overdose.

In another aspect of the present invention, there is provided a series of haptens designed for generating class-specific monoclonal antibody that could be used as a pharmacokinetic antagonist for treating the medical problems associated with abuse of methamphetamine-like stimulants.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 1 shows the use of a long-acting anti-METH antibody medication for the treatment of drug addiction. In this clinical scenario, the patient has entered a drug treatment program for d-methamphetamine addiction and they are treated with a long acting anti-methamphetamine monoclonal antibody-based medication. In this example, the prototype long acting antagonist is an IgG antibody.

FIG. 2 shows the use of short-acting anti-methamphetamine monoclonal antibody fragment to treat an overdose resulting from d-amphetamine-like drugs. In this case d-methamphetamine is used as the prototype drug and an anti-methamphetamine monoclonal Fab is used as the antibody-based medication.

FIG. 15 shows the results from treatment of a methamphetamine-induced overdose in rats with a monoclonal anti-methamphetamine antibody or anti-phencyclidine monoclonal antibody (a control monoclonal antibody that does not bind amphetamine like drugs). Rats (n=4 per group) were administered saline (left most bar) or 1.0 mg/kg d-methamphetamine as an intravenous bolus dose. When drug effects were maximizing at 30 minutes, they were treated with saline (control), an anti-phencyclidine monoclonal antibody Fab fragment (anti-PCP), or an anti-d-methamphetamine-specific monoclonal antibody Fab fragment (anti-methamphetamine).

DETAILED DESCRIPTION OF THE INVENTION

Figure 1A:
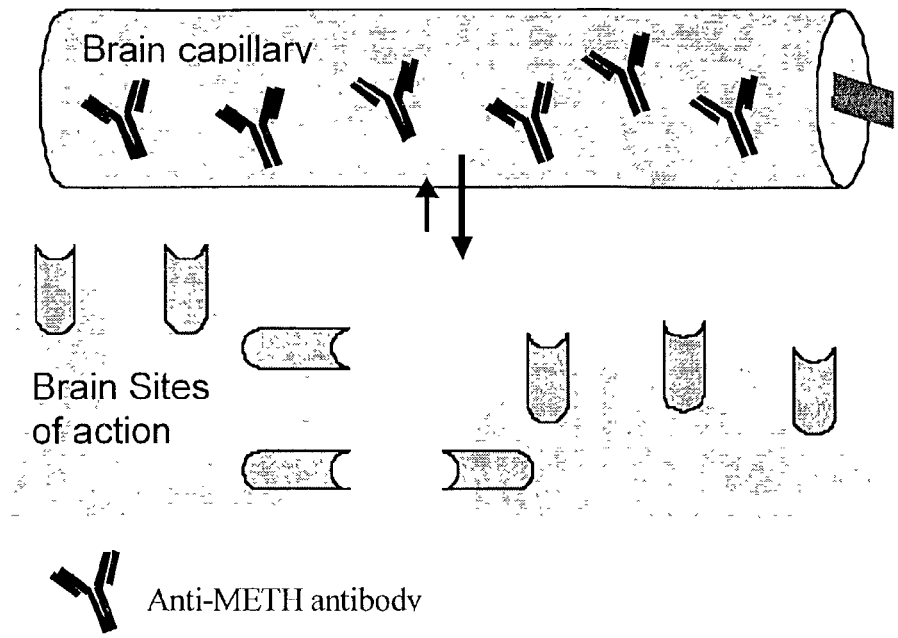
FIG. 1A shows the patient's brain after receiving a dose of a long-acting anti-METH antibody when they enter into a drug treatment program. This medication will serve as a treatment to help prevent or blunt the rewarding effects of amphetamine-like drug usage by the recovering addict.
Figure 1B:
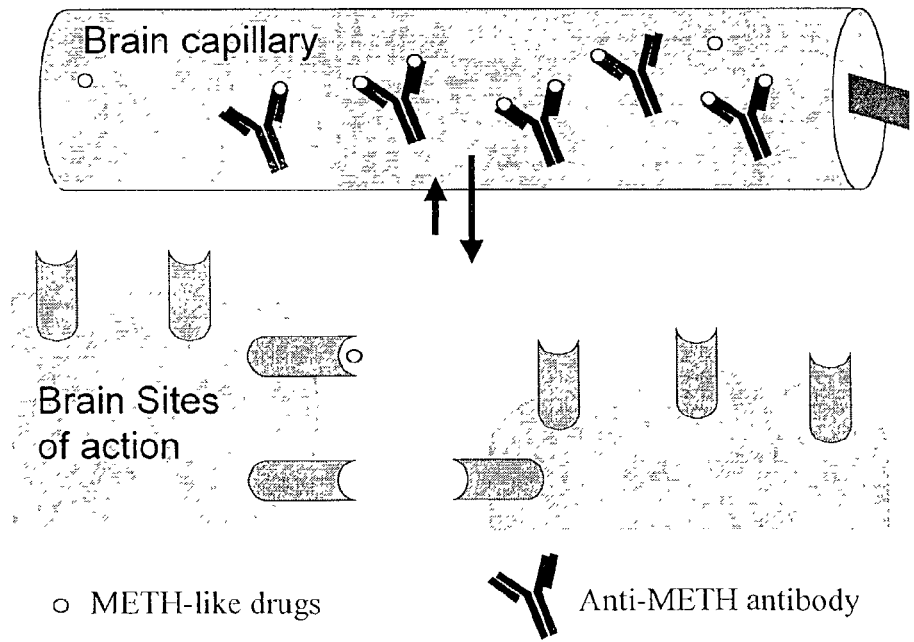
FIG. 1B shows after the patient is pre-treated with the anti-methamphetamine antibody medication, accidental or purposeful use of d-amphetamine-like drugs by the patient will be blocked or at least significantly blunted. Thus, the drug(s) can not reach their site of action in the central nervous system. This will prevent the patient from feeling the reinforcing effects of drug use, and aid in the prevention of relapse.
Figure 2A:
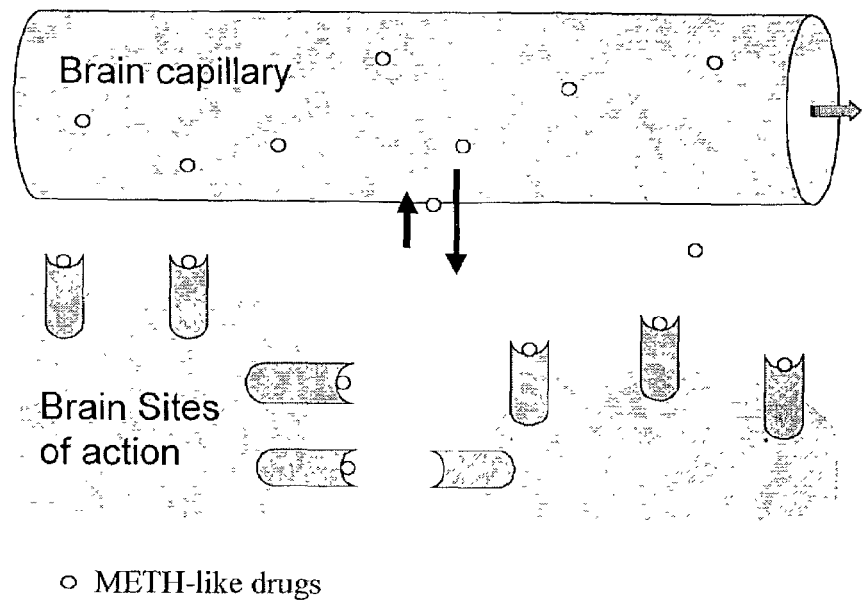
FIG. 2A shows that before the treatment with anti-METH antibody medication, the patient arrives in an emergency room with a high body burden of methamphetamine. This drawing shows that brain concentrations are very high and the drug is occupying drug sites of action in the patient's brain. This is producing the clinical overdose.
Figure 2B:
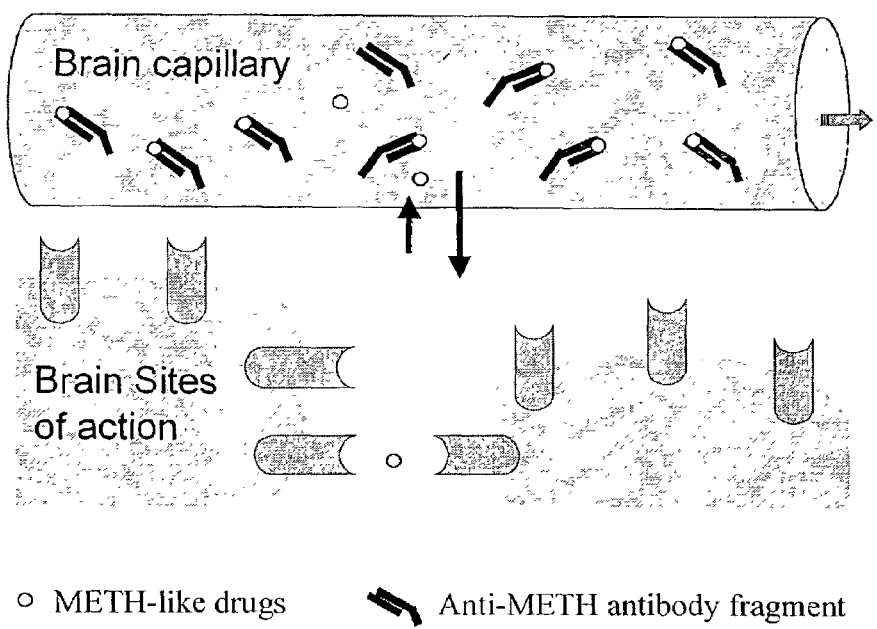
FIG. 2B shows after treatment with anti-methamphetamine antibody fragments, the drug is rapidly removed from the brain and the patient quickly recovers. In this example, the prototype short acting antibody based medication is anti-methamphetamine antibody fragments

This invention encompasses a method of generating high affinity monoclonal antibodies and their antigen binding fragments (e.g., Fab) for use in treating the medical problems associated with stimulant drug abuse. d-Methamphetamine is the prototypic stimulant molecule because it has severe addiction liability and produces significant acute and chronic medical problems. Anti-methamphetamine monoclonal antibody (of any mammalian source) can be used as a prototypic, long acting stimulant antagonist for treating addiction (FIG. 1). In contrast, smaller molecular weight fragments (like Fab) can be used as a prototypic shorter acting, less antigenic, more rapidly eliminated antagonist for treating drug overdose (FIG. 2). Since intact antibody and smaller fragments like Fab are cleared by different organ systems, this approach will also provide a greater potential for altering and controlling the endogenous clearance and biological safety of these proteins.

The current studies disclose the development of anti-d-methamphetamine monoclonal antibodies (mAb) and test the mAb-based therapy in a rat model of d-methamphetamine ((+)-METH) overdose. For all studies, the dose of monoclonal antibody was equimolar in binding sites to the body burden of a 1-mg/kg intravenous (+)-METH dose at 30 min. The results showed that a (+)-METH-specific, high-affinity murine mAb ($k_d$=11 nM) was 2–3 times more effective than a low-affinity mAb ($k_d$=250 nM) at antagonizing (+)-METH-induced locomotor effects. The high-affinity mAb completely reversed locomotor effects produced by 0.3 mg/kg dose of (+)-METH and decreased effects due to 1 mg/kg dose by >60–70%. It was also shown that anti-(+)-METH mAbs antagonize (+)-METH effects by altering brain distribution of (+)-METH. For these studies, rats received 1 mg/kg (+)-METH followed by no treatment (control group) or the mAb at 30 min. The areas under the (+)-METH concentration-versus-time curves showed that the mAb increased the serum area by >9,000% and decreased the brain area by >70%. (+)-Amphetamine serum and brain concentrations were only minimally affected.

Drugs can function as discriminative stimuli to control responding. This function may overlap with the reinforcing stimuli that are produced by the drugs, which in turn can contribute to their self administration and abuse liability. Some investigators suggest that the discriminative stimulus properties of drugs may be related to their subjective effects in humans, although evidence suggests that this relationship is complicated. The discriminative stimulus effects of a drug are often shared among drugs that produce similar pharmacological effects; and some investigators suggest that the shared discriminative-stimulus effects of drugs can be used to define drug classes. For these reasons, drug discrimination has been of great interest to drug abuse researchers.

If the mAbs disclosed herein bind to d-methamphetamine with high affinity, they should prevent the drug from penetrating into the central nervous system to produce its discriminative stimulus effects. If an anti-d-methamphetamine antibody could alter the d-methamphetamine dose-response curve for the discriminative stimulus effects of d-methamphetamine, it would suggest possible therapeutic usefulness of antibody treatment for methamphetamine abuse.

Rats and pigeons were trained to discriminate (+)-methamphetamine (rats), cocaine (rats), or (+)-amphetamine (pigeons) from saline after which dose-response curves were determined for (+)-methamphetamine and other drugs before and after administration of a (+)-methamphetamine specific monoclonal antibody ($K_D$=250nM). Intravenous (+)-methamphetamine was about 3 times more potent as a discriminative stimulus in rats than intraperitoneal (+)-amphetamine. Also in rats, (+)-methamphetamine and (+)-amphetamine were about equipotent as discriminative stimuli and were about 3 times more potent than cocaine. In pigeons, (+)-methamphetamine and (+)-amphetamine were nearly equipotent, while cocaine was slightly less potent. In rats, administration of 1 g/kg of the antibody shifted both intravenous and intraperitoneal dose-response curves for (+)-methamphetamine discrimination approximately 3-fold to the right for up to 7 days. A similar shift of approximately 3-fold to the right that lasted for at least 7 days occurred when the 1 g/kg dose of the antibody was given to pigeons. The antibody did not affect the (+)-amphetamine or cocaine dose-response curves. The effects of a second (+)-methamphetamine monoclonal antibody ($K_D$=10 nM) also were studied in both rats and pigeons. The higher affinity antibody produced a 3–10 fold shift to the right of the (+)-methamphetamine dose-response curve for drug discrimination in both species. These data showed that (+)-methamphetamine-specific antibodies can produce an antagonism of an effect of (+)-methamphetamine that is closely associated with its abuse.

As used herein, the term "monoclonal antibody" means an antibody composition recognizing a discrete antigen determinant. It is not intended to be limited with regard to the source of the antibody or the manner in which it is made. The term antibody is also intended to encompass whole antibodies, biologically functional fragments thereof, chimeric and humanized antibodies comprising portions from more than one species, or other molecules whose binding properties are derived from antibody-like high affinity binding sites.

In this instance, monoclonal antibodies were produced by hybridomas. However, monoclonal Fab fragments and IgG fragments can also be produced by other methods, for example by using bacteriophage to display and select polypeptide chains expressed from a V-gene library or genetic engineering.

Biologically functional antibody fragments are those fragments sufficient for binding to the desired stimulant drug, such as Fab, Fv, F(ab')$_2$, and sFv (single-chain antigen-binding protein) fragments. One can choose among these or whole antibodies for the properties appropriate to a particular method.

Chimeric antibodies can comprise proteins derived from two different species. The portions derived from two different species can be joined together chemically by conventional techniques or can be prepared as a single contiguous protein using genetic engineering techniques (See e.g. Cabilly et al., U.S. Pat. No. 4,816,567; Neuberger et al., WO 86/01533 and Winter, EP 0,239,400). Such engineered antibodies can be, for instance, a chimeric antibody comprising murine variable regions and human constant regions, or complementarity determining regions (CDR)-grafted antibodies (Tempest et al., 1991). The constant region domains can be chosen to have an isotype most suitable for the intended application of the antibodies.

It is contemplated that pharmaceutical compositions may be prepared using the antibodies of the present invention. In such a case, the pharmaceutical composition comprises the monoclonal antibodies or antigen-binding fragments thereof of the present invention and a pharmaceutically acceptable carrier. The present invention has included the calculation and administration of equimolar amount of antibodies, and a person having ordinary skill in this art would readily be able to determine, without undue experimentation, the appropriate dosages and routes of administration of the monoclonal antibodies of the present invention. When used in vivo for therapy, the monoclonal antibodies of the present invention are administered to the patient or an animal in therapeutically effective amounts, i.e., amounts that eliminate or reduce the effects of stimulant drug overdose or abuse.

In addition to the obvious benefits of a new therapeutic approach, other important contributions would be derived from the present invention. In as much as the binding properties of receptors and antibodies are similar in many ways, the careful design of amphetamine-like haptens could lead to the selection of antibodies that mimic aspects of the endogenous binding sites of these drugs in the CNS. Molecular studies of these antibody binding sites (through protein sequencing, structure-activity studies and molecular modeling) could aid in the prediction of the characteristics necessary for drug-receptor interaction including neuronal transporters, vesicular storage systems, and with monoamine oxidase. Molecular studies of the sequence of the antibody binding site and the neuronal transporters may also yield important clues concerning the structural rules for molecular interactions of biologically active compounds. Furthermore, the use of these antibody models for screening peptide and organic combinatorial libraries could lead to discovery of novel agonists or antagonists for these neuronal transporters.

The present invention is directed to a monoclonal antibody or an antigen binding fragment thereof that specifically recognizes a stimulant drug of abuse or a metabolite thereof. Representative drugs of abuse or such metabolites include d-methamphetamine, d-amphetamine, 3,4-methylenedioxymeth-amphetamine, 3,4-methylenedioxyamphetamine and structural-related analogs of these compounds. In one form, the antibody is of murine origin. Alternatively, the antibody is of human origin or contains portions of a human antibody.

As used herein, "structural-related analogs" refers to any known or unknown chemical moiety (including drug metabolites) that has a similar chemical structure, and similar pharmacological effects (e.g., behavioral and receptor binding effects) to other known D-methamphetamine-like drugs. For example, phencyclidine (a different drug of abuse) has structurally related analogs like N-ethyl-1-phenylcyclohexylamine (PCE) and 1-[1-(2-thienyl]piperidine (TCP), which are also drugs of abuse (see Owens et al. 1988 for a similar discussion for developing anti-PCP antibodies which recognize structural and pharmacologic similarities in drugs of abuse). Morphine has structurally related analogs like heroin, which is also abused. Fentanyl has a number of structurally related analogs, which have been used as drugs of abuse. In the cases phencyclidine and fentanyl these structurally related drugs are sometimes referred to as designer drugs, because they mimic the effects which are desired by drug abusers.

The present invention also provides methods of treating stimulant drug abuse or overdose, comprising the step of administering a pharmacological effective dose of the monoclonal antibody or an antigen binding fragment thereof of the present invention to an individual in need of such treatment. Representative stimulant drugs are described above.

The present invention is also directed to a compound with the structure of

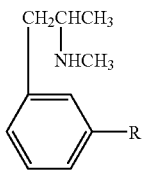

where R is a linker group substituted on the aromatic ring at one of C2, C3 or C4; where R is —$ZR_2COOR$,; Z is O, S or a single bond between $R_2$ and one of C2, C3 or C4; $R_1$ is H or $R_4$; $R_2$ is a $C_{2-9}$ alkyl, alkenyl or alkynyl chain, said alkyl chain optionally containing an O or a $NR_3$ moiety; $R_3$ is $C_{1-5}$ alkyl; $R_4$ is —$CH_2CH_2CN$, 4-nitrophenyl, 2,3,4,5,6-pentafluorophenyl; succinimide, or

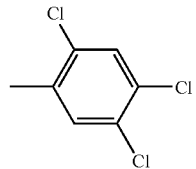

(2,3,5-trichlorophenyl) or a hydrochloride salt of said substituted methamphetamine. This compound can possess either (S)- or (R)-stereochemistry. In embodiments of this invention the substituted methamphetamines can have substituents as shown in Table 1. A preferred embodiment is (S)- or (R)-3-(5'-carboxypentyloxy) methamphetamine hydrochloride.

TABLE 1

| R | x | y |
|---|---|---|
| $O(CH_2)_xCOOH$ | 2–9 | n/a |
| $OCH_2CH=CH(CH2)_xCOOH$ | 1–6 | n/a |
| $OCH_2C\equiv C(CH2)_xCOOH$ | 1–6 | n/a |
| $O(CH_2)_xO(CH2)_yCOOH$ | 2–4 | 1–5 |
| $O(CH_2)_xNR3(CH2)_yCOOH$ | 2–3 | 1–5 |
| $S(CH_2)_xCOOH$ | 2–9 | n/a |
| $SCH_2CH=CH(CH2)_xCOOH$ | 1–6 | n/a |
| $SCH_2C\equiv C(CH2)_xCOOH$ | 1–6 | n/a |
| $S(CH_2)_xO(CH2)_yCOOH$ | 2–4 | 1–5 |
| $S(CH_2)_xNR3(CH2)_yCOOH$ | 2–3 | 1–5 |
| $(CH_2)_xCOOH$ | 3–8 | n/a |
| $(CH_2)_xCH=CHCOOH$ | 2–7 | n/a |
| $(CH_2)_xC\equiv CCOOH$ | 2–7 | n/a |
| $CH=CH(CH2)_xCOOH$ | 1–6 | n/a |
| $C\equiv C(CH2)_xCOOH$ | 1–6 | n/a |

The present invention is also directed to a method of generating a class-specific monoclonal antibody that recognizes methamphetamine-like stimulants, comprising the step of: immunizing animals with the substituted methamphetamines or hydrochlorides thereof disclosed herein.

The following examples are given for the purpose of illustrating various embodiments of the invention and are not meant to limit the present invention in any fashion.

EXAMPLE 1

Generation of High Affinity Monoclonal Antibodies and Fab Fragments that Bind to D-Methamphetamine and other Stimulant Drugs The haptens are coupled to a bovine serum albumin antigen by using a general synthesis procedure (Minh-Tam et al., 1981). This two-step, modified carbodiimide procedure permits a defined number of haptens to be covalently bound to the protein in a controlled molecular orientation. It also minimizes cross linking of protein molecules and the unwanted conjugation of the haptens through the free amino group on the d-methamphetamine haptens. A complimentary ovalbumin-d-methamphetamine hapten was also generated for use in screening hybridoma products in an enzyme-linked immunosorbent assay (ELISA). This general synthesis procedure has been used in the past to generate anti-drug antibodies (Owens et al., 1988) and anti-peptide antibodies (Laurenzana et al., 1995).

For the production of monoclonal antibodies, BALB/c mice (n=6–10 per hapten) are immunized with 100 μg of the BSA-d-methamphetamine, emulsified in an equal volume of an adjuvant (e.g., Titer Max, RIBI, Freund's Complete Adjuvant). One month later the animals were boosted with the same reagents and two weeks later the serum was tested for specific antibodies using the ovalbumin-d-methamphetamine conjugates in an ELISA. The spleen from the animal with the highest titer of anti-d-methamphetamine antiserum was used for the first fusion. The other animals were boosted every three to four weeks to maintain titers of anti-d-methamphetamine in anticipation of future immunizations. After fusion of spleen cells from the mice with a myeloma cell line, hybridomas secreting anti-d-methamphetamine antibodies were identified using an ELISA with the appropriate ovalbumin-d-methamphetamine conjugate as described (Laurenzana et al., 1995).

Wells with a positive reaction to d-methamphetamine were subcloned to monoclonality. For specificity determinations, the antibodies were tested in an ELISA format using a series of ligands. These ligands include (but are not limited to) d- and l-methamphetamine, d- and l-amphetamine, MDMA, MDA, ephedrine, pseudoephedrine, and other potentially cross reacting stimulant-like molecules and endogenous neurotransmitters. Antibodies specific for the d-isomers and having a low Kd value (e.g., <1–30 nM) were selected. Although a range of antibody affinities (as great as 250 nM) has been studied, the objective was to have affinity constants for methamphetamine in the range of 1–30 nM.

Once an anti-d-methamphetamine secreting hybridoma was chosen, large quantities of the antibody were produced in a hollow fiber bioreactor (Valentine and Owens, 1996). A representative method for the monoclonal antibody purification process is as follows. Monoclonal antibody-containing tissue culture media was combined and concentrated to one-tenth of the original volume using an Amicon spiral cartridge concentration system. This technique takes approximately 10 minutes to concentrate 2 L down to 100–200 ml. The procedure recovers 95% of the monoclonal antibody and removes >95% of the bovine albumin in the media. The concentrated monoclonal antibody was dialyzed against 50 mM MES buffer (2-(N-Morpholino)-ethane-sulfonic acid), pH 6.0 for further purification using a large, glass chromatography column packed with 1L of SP-Sepharose Big Bead media (Pharmacia LKB Biotechnology). The sample was loaded on the column and washed with the MES buffer to remove non-specifically bound proteins. The monoclonal antibody was eluted in one step using 50 mM MES/0.15 M NaCl. This elution also serves to reconcentrate the monoclonal antibody. The purity and concentration of the purified anti-d-methamphetamine monoclonal antibody were determined by SDS-PAGE and spectrophotometry respectively.

Fab fragments of the monoclonal antibody were produced by the papain digestion method described by Goding (1983) using an mAb:papain ratio of 500:1 (w/w). After digestion, the Fab was purified using a HPLC column containing Pharmacia Streamline DEAE Sepharose anion exchange media. Purity was checked by SDS-PAGE and the protein concentration was measured with a Coomassie protein assay or spectrophotometrically. For every 100 g of monoclonal antibody, one may expect to yield at least 55–68 g of Fab fragments. For use in animals, the Fab and monoclonal antibody were dialyzed against PBS, pH 7.4 and concentrated with an Amicon ultrafiltration device to 50–100 mg/ml (depending on the needs of the in vivo testing procedure). Both Fab and monoclonal antibody were stored at −80° C. until needed. There was no decrease in binding activity or solubility after long-term storage of the monoclonal antibody or Fab.

EXAMPLE 2

Synthesis of Hapten

Figure 3:
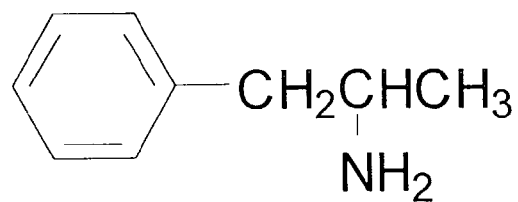
FIG. 3 shows the structures of methamphetamine-like stimulants.
Figure 3:
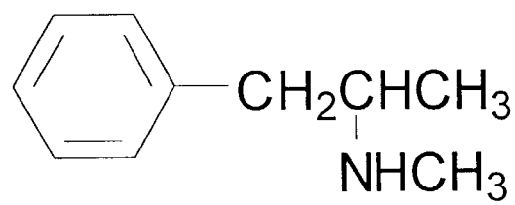
Figure 3:
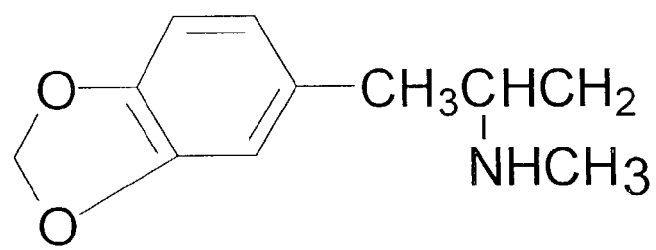
Figure 4A:
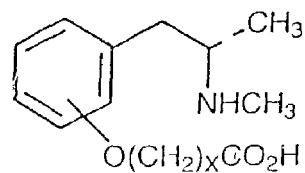
FIGS. 4A–4C show the hapten 10 to hapten 24 designed for generating antibodies that are specific for methamphetamine-like stimulants.
Figure 4A:
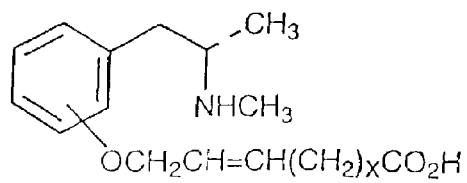
Figure 4A:
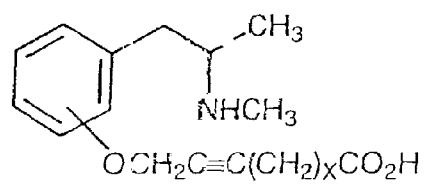
Figure 4A:
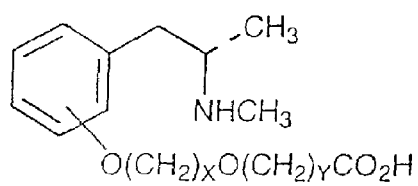
Figure 4A:
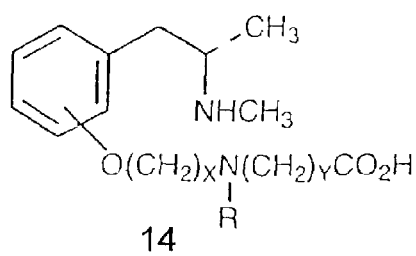
Figure 4B:
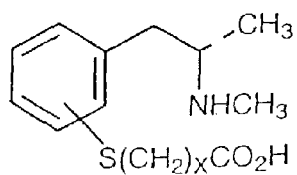
Figure 4B:
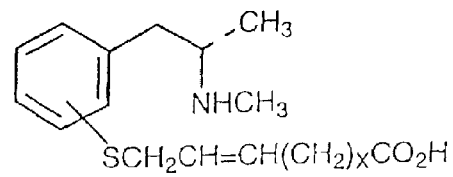
Figure 4B:
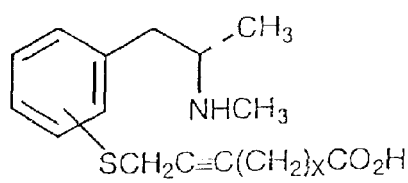
Figure 4B:
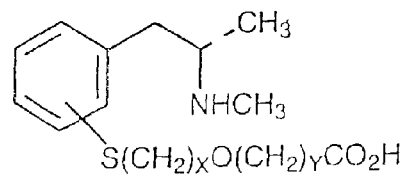
Figure 4B:
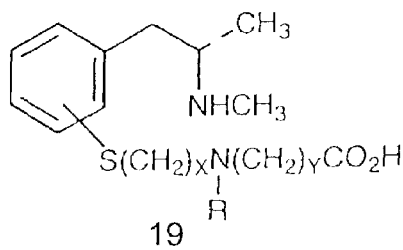
Figure 4C:
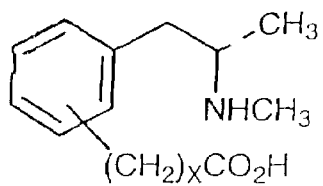
Figure 4C:
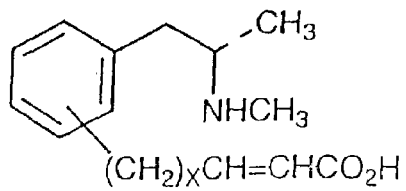
Figure 4C:
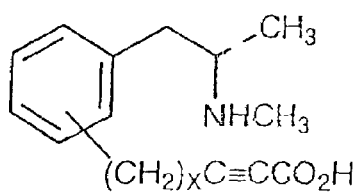
Figure 4C:
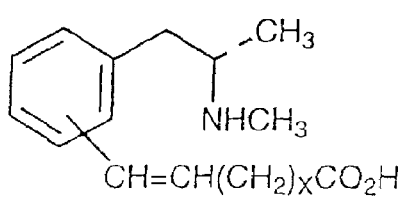
Figure 4C:
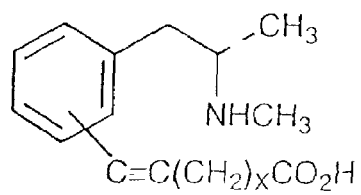

One goal of the present invention was to generate a class-specific monoclonal antibody that could be used as a pharmacokinetic antagonist for treating the medical problems associated with methamphetamine-like stimulants. The methamphetamine-like stimulants that are most often abused are methamphetamine, amphetamine and MDMA (FIG. 3). Based on review of the literature on anti-methamphetamine antibodies (e.g., Faraj et al., 1976; Usagawa et al., 1989; Ward et al., 1994) and analysis of the molecular features of the molecules shown in FIG. 3, it is hypothesized that coupling of a spacer group (with a carboxylic acid terminus) at the para or meta position of the aromatic ring structure will offer the best chance for generating a class-specific antibody. The resulting antibodies are expected to react best with the parent compound, as opposed to metabolites, and would also be less likely to significantly cross react with natural neurotransmitters. If the protein was coupled to the amine groups at the other end of the molecule (which would be more convenient), this would not generate antibodies that would cross react with MDMA. The haptens designed for generating antibodies specific for methamphetamine-like stimulants are illustrated in FIGS. 4A–4C.

Figure 5:
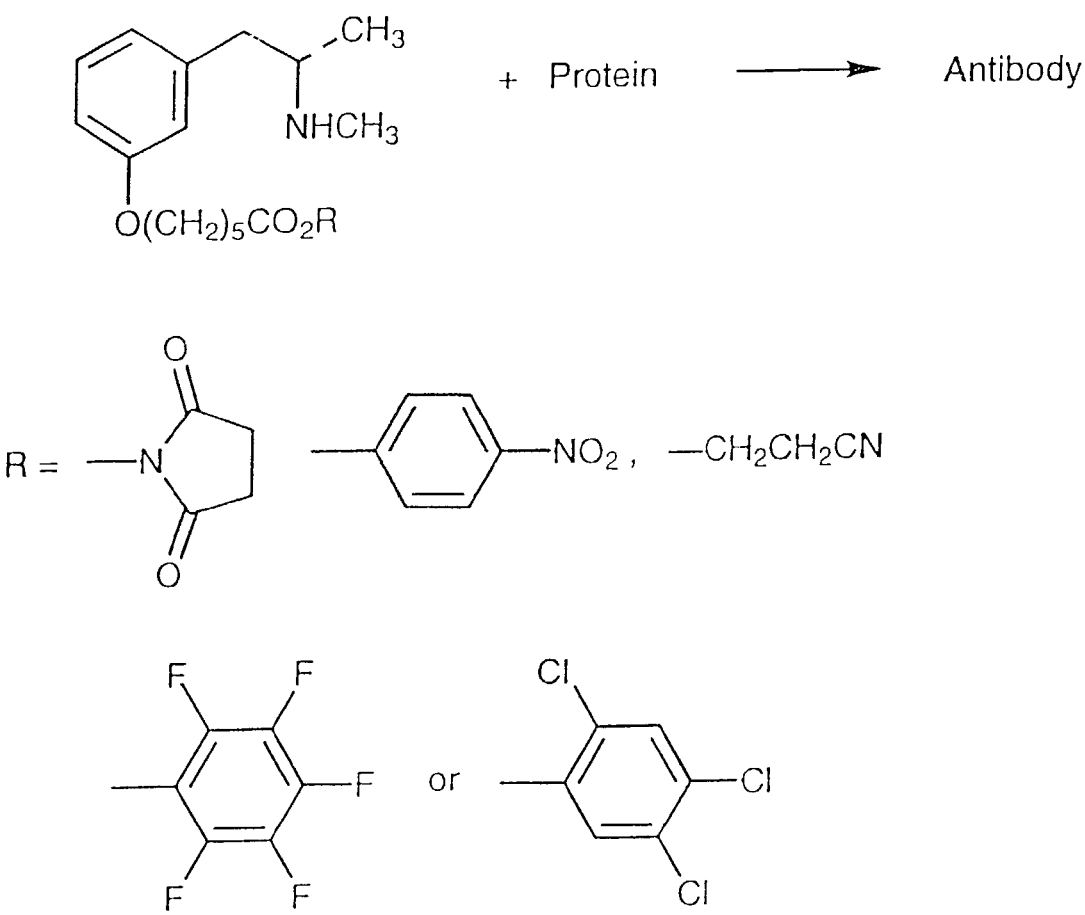
FIG. 5 shows a method of using activated ester to couple the hapten to a protein to make the antibody. Similar chemistry would apply to all other structures shown in FIGS. 4A–4C.

A method of using activated ester to couple the hapten to a protein to make the antibody is shown in FIG. 5. Similar chemistry would apply to all other structures shown in FIGS. 4A–4C.

Figure 6:
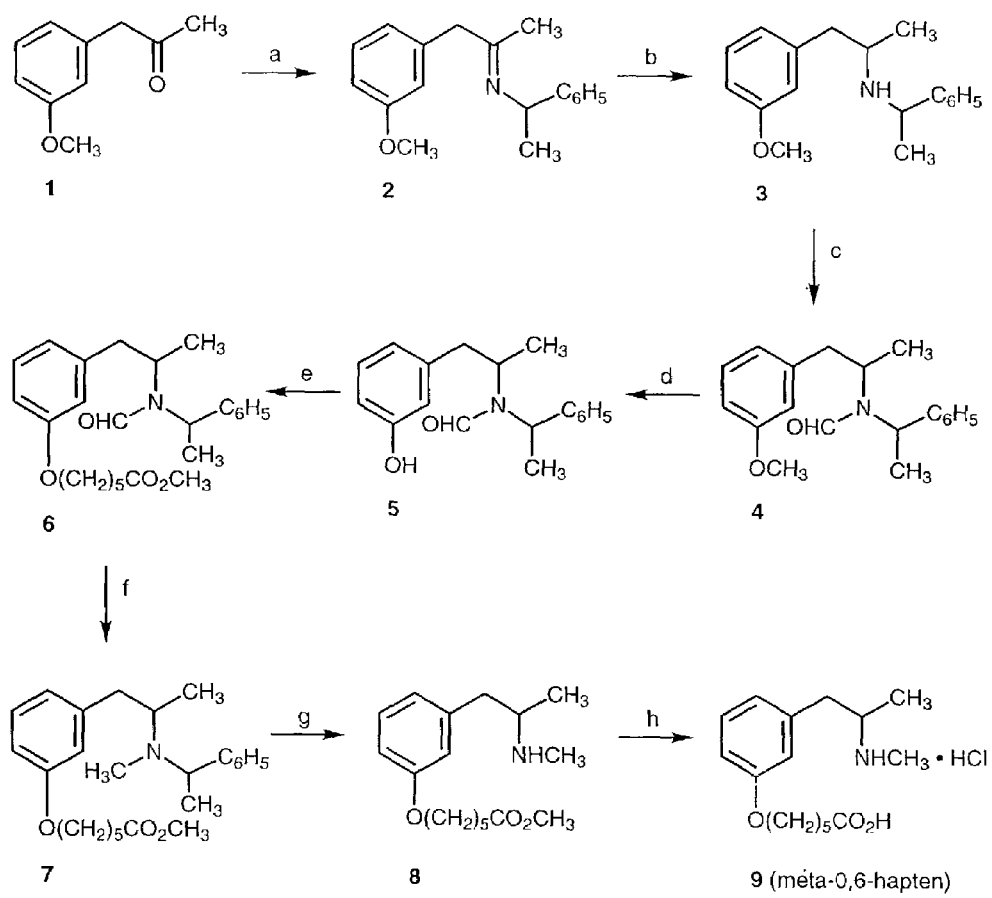
FIG. 6 shows the scheme of synthesis for 3-(5'-carboxypentyloxy)methamphetamine hydrochloride.

The synthesis of one of the haptens (hapten 1 in FIG. 4A with X=5 and connected at the 3-position) is outlined in FIG. 6. The goal is to prepare the (S)-(+)-isomer of 3-(5′-carboxypentyloxy)methamphetamine (9). To establish the feasibility of the synthetic methods, the synthesis of (R)-(−)-9 is presented. Those skilled in the art will know that (S)-(+)-9 can be prepared using exactly the same method starting with (S)-α-methylbenzylamine.

Thus, to prepare (R)-9, 3-methoxyphenylacetone (1) was condensed with (R)-α-methylbenzylamine to give 2. Raney nickel reduction of 2 followed by separation provided the pure (R,R)-diastereoisomer 3. The N-formyl-protected intermediate 4 was obtained by treating 3 with a formic acid-acetic anhydride mixture. O-Demethylation of 4 using boron tribromide yielded the phenol 5. Alkylation of 5 with methyl 6-bromohexanoate afforded 6. Reduction of 6 using diborane provided the N—CH$_3$ intermediate 7, which yielded 8 on reduction using palladium on carbon catalyst in refluxing formic acid. The desired final optically pure hapten 9 as the hydrochloride salt was obtained by treating 8 with dilute hydrochloric acid.

EXAMPLE 3

Synthesis of (R,R)-N-α-Methylbenzyl-3-Methoxyamphetamine Hydrochloride

A solution of 3-methoxyphenylacetone (10 g, 0.061 mol) and (R)-α-methylbenzylamine (7.38 g, 0.061 mol) in 100 mL of dry toluene was heated to reflux in a flask fitted with a Dean-Stark condenser for 20 h. After cooling the reaction mixture, the solvent was removed, and the residue was dried under vacuum. The residual oil was dissolved in absolute EtOH (60 mL), and a slurry of EtOH washed Raney nickel was added. The resulting mixture was hydrogenated for 96 h at 40 psi hydrogen. The catalyst was removed by filtration over a Celite bed, and the filtrate was treated with HCl gas. Evaporation of the solvent gave a white solid which was triturated with hot acetone to provide the target compound 3 as a white solid. An analytical sample was prepared from an aliquot removed. The sample recrystallized from MeOH/diethyl ether had mp 215–218° C.; [α]$^{21}$D (17.85°, c 1.95, MeOH). $^1$H NMR (CD$_3$OD) δ 1.17 (d, 3H), 1.69 (d, 3H), 2.53 (dd, 1H), 3.17 (m, 1H), 3.31 (m, 1H), 3.74 (s, 3H), 4.63 (q, 1H), 6.59 (s, 1H), 6.62 (d, 1H), 6.82 (d, 1H), 7.21 (t, 1H), 7.54 (m, 5H). Elemental analysis: calcd. for C$_{18}$H$_{23}$NO.HCl: C, 70.69; H, 7.91; N, 4.58; Cl, 11.59. Found: C, 70.51; H, 7.99; N, 4.53; Cl, 11.65.

EXAMPLE 4

Synthesis of (R,R)-N-formyl-N-α-methylbenzyl-3-methoxyamphetamine

To a stirred solution of formic acid (7.5 mL, 0.2 mol) at 0° C. was added acetic anhydride (18.9 mL, 0.2 mol) dropwise. After 30 min, the amine 3 (3.9 g, 13.7 mmol) in a minimum volume of formic acid was added, and the mixture was stirred overnight. Water was carefully added, and the mixture was neutralized with dilute NH$_4$OH. The mixture was extracted with CH$_2$Cl$_2$, washed with saturated sodium chloride solution, and dried over NaSO$_4$. The residue obtained after evaporation was purified on a silica gel column eluting with a solvent mixture of hexane/CH$_2$Cl$_2$/CH$_3$OH (5:14:1) to give 3.83 g (94%) of 4 as a white solid.

EXAMPLE 5

Synthesis of (R,R)-N-formyl-N-α-methylbenzyl-3-hydroxy amphetamine

To a stirred solution of 4 (2.85 g, 10 mmol) in CH$_2$Cl$_2$ (30 mL) was added a solution of BBr$_3$ (4.84 g, 20 mmol) in 50 mL of CH$_2$Cl$_2$. After stirring overnight, the excess of BBr$_3$ was quenched by careful addition of water and the organic fraction separated. The aqueous layer was further extracted with CH$_2$Cl$_2$, and the combined CH$_2$Cl$_2$ fraction was dried over Na$_2$SO$_4$. Evaporation gave 2.01 g (74%) of 5 as a white solid. Further purification on a silica gel column eluting with hexane/CH$_2$Cl$_2$/MeOH (4:8:1) gave 1.65 g (61%) pure product. The analytical sample was triturated with ether to give white crystals; mp 174–177° C. Elemental analysis: calcd. for $C_{18}H_{21}NO_2 \cdot 1.25 H_2O$: C, 75.69; H, 7.50; N, 4.91. Found: C, 75.67; H, 7.46; N, 5.00.

EXAMPLE 6

Synthesis Of (R)-3-(5'-carbomethoxypentyloxy) methamphetamine

To a suspension of hexane washed sodium hydride (216 mg, 4.32 mmol) in 5 mL of DMF was added a solution of (R,R)-3-hydroxyphenyl-2-propyl-N-formamido-N-α-methylbenzylamine (5) (1.22 g, 4.32 mmol). After stirring for 30 min at room temperature, a solution of methyl 6-bromohexanoate (1.36 g, 6.48 mmol) in DMF (3 mL) was added and stirred overnight at room temperature. The reaction mixture was diluted with $H_2O$ (50 mL) and extracted with methylene chloride (3×10 mL). The combined organic fraction was washed with saturated sodium chloride solution and dried over $Na_2SO_4$. After removal of the solvent, the residue was purified on a silica gel column. Eluting with a solvent mixture ($CH_2Cl_2$:hexane:MeOH, 4:14:1) to give 1.68 g (95%) of 6. $^1H$ NMR ($CDCl_3$) δ 1.28 (dd, 3H), 1.53 (m, 2H), 1.58 (dd, 3H), 1.72 (m, 4H), 2.36 (m, 2H), 2.41 (m, 1H), 2.89 (m, 1H), 3.25 (m, 1H), 3.41 (t, 2H), 3.68 (s, 3H), 3.82 (q, 2H), 4.58, 6.07 (2 q, 1H), 6.17, 6.67 (2 s, 1H), 6.57, 6.40 (2d, 1H), 6.67 (dd, 1H), 7.05 (dd, 1H), 7.36 (m, 5H), 8.41, and 8.48 (two s, 1H). The sample was used in the next step without further characterization.

A solution of the above formamide 6 (1.63 g) was treated with $BH_3 \cdot THF$ (10 mL) and stirred for 30 min when the excess of $BH_3$ was decomposed with MeOH followed by dilute HCl. The reaction mixture was basified with dilute $NH_4OH$ and extracted with methylene chloride (3×25 mL). The organic fraction was dried over $Na_2SO_4$ and evaporated to dryness. The oily material was dissolved in MeOH (25 mL), and Pd/C (250 mg) was added. The mixture was heated to reflux with formic acid (3 mL in three portions) for an hour. The filtrate, obtained after removal of the catalyst, was evaporated and the resulting residue purified on a silica gel column. Elution with 10% MeOH in methylene chloride gave 0.84 g (70% overall in two steps) of a clear oil 8. $^1H$ NMR ($CDCl_3$) 1.06 (d, 3H), 1.50 (m, 2H), 1.71 (m, 2H), 1.80 (m, 2H), 2.33 (t, 2H), 2.41 (s, 3H), 3.67 (s, 3H), 3.95 (t, 2H), 6.75 (m, 3H), 7.19 (m, 1H). The sample was converted to HCl salt; mp 53–57° C. Elemental analysis: calcd. for $C_{17}H_{27}NO_3 \cdot HCl \cdot 0.75 H_2O$: C, 59.50; H, 8.50; N, 4.10. Found: C, 59.65; H, 8.45; N, 4.21.

EXAMPLE 7

Synthesis Of (R)-3-(5'-carboxypentyloxy)methamphetamine hydrochloride

A solution 8 (400 mg, 1.15 mmol) in dilute hydrochloric acid (6N, 5 mL) was heated to reflux for 4 h. The reaction was evaporated to dryness, and the residue was crystallized from MeOH/ether to give 215 mg (59%) of an off-white crystalline material: mp 73–77° C. $^1H$ NMR ($CD_3OD$) 1.25 (d, 3H), 1.34 (m, 2H), 1.40 (m, 2H), 1.67 (m, 2H), 2.65 (t, 2H), 2.72 (s, 3H), 4.22 (m, 2H), 6.73 (m, 3), 7.13 (s, 1H). Elemental Analysis: calcd. for $C_{16}H_{25}NO_3 \cdot HCl \cdot 0.25 H_2O$: C, 59.99; H, 8.34; N, 4.37; Cl, 11.07. Found: C, 60.09; H, 8.33; N, 4.37; Cl, 11.13.

EXAMPLE 8

Effect Of Hapten Design On Antibody Specificity For D-Methamphetamine Like Drugs In these experiments, rabbit antiserum was generated against two unique d-methamphetamine like haptens. Each hapten included the basic chemical structure of d-methamphetamine, along with a new chemical linker group attached at the para (para-O,6 hapten) or meta (meta-O,6 hapten) positions of the aromatic ring structure. The distal end of this linker group had a carboxy terminus for use in forming a peptide bond with protein antigens. After synthesis of a hapten-bovine serum albumin conjugate, this antigen was used for immunizing two rabbits. The first immunization for each rabbit was with 200 μg of either para-O,6 antigen or meta-O,6 antigen in Freund's complete adjuvant. The first booster immunization was with 100 μg of antigen in Freund's incomplete adjuvant. Seven to ten days later each animal was bled and the serum was collected for testing.

After titering each antiserum for selection of an appropriate serum dilution for radioimmunoassay, the relative cross-reactivity of each antiserum was determined. In this assay, a constant dilution of antiserum and a constant amount of [$^3H$]-methamphetamine was added to each test tube. Next, increasing amounts of either d-amphetamine or d-methamphetamine were added to separate tubes. After an overnight incubation at 4–8° C., the antibody bound [$^3H$]-methamphetamine was separated from the free [$^3H$]-methamphetamine using a goat anti-rabbit second antibody. The antibody precipitate in each tube was then transferred to a scintillation vial and the amount of radioactivity in each tube was determined by liquid scintillation spectrometry. For each of the test drugs (either d-amphetamine or d-methamphetamine), the $ED_{50}$ value for inhibition of [$^3H$]-methamphetamine binding to each antiserum was determined using a sigmoidal (logistic) fit to the percentage of [$^3H$]-methamphetamine binding versus log ligand dose.

Figure 7:
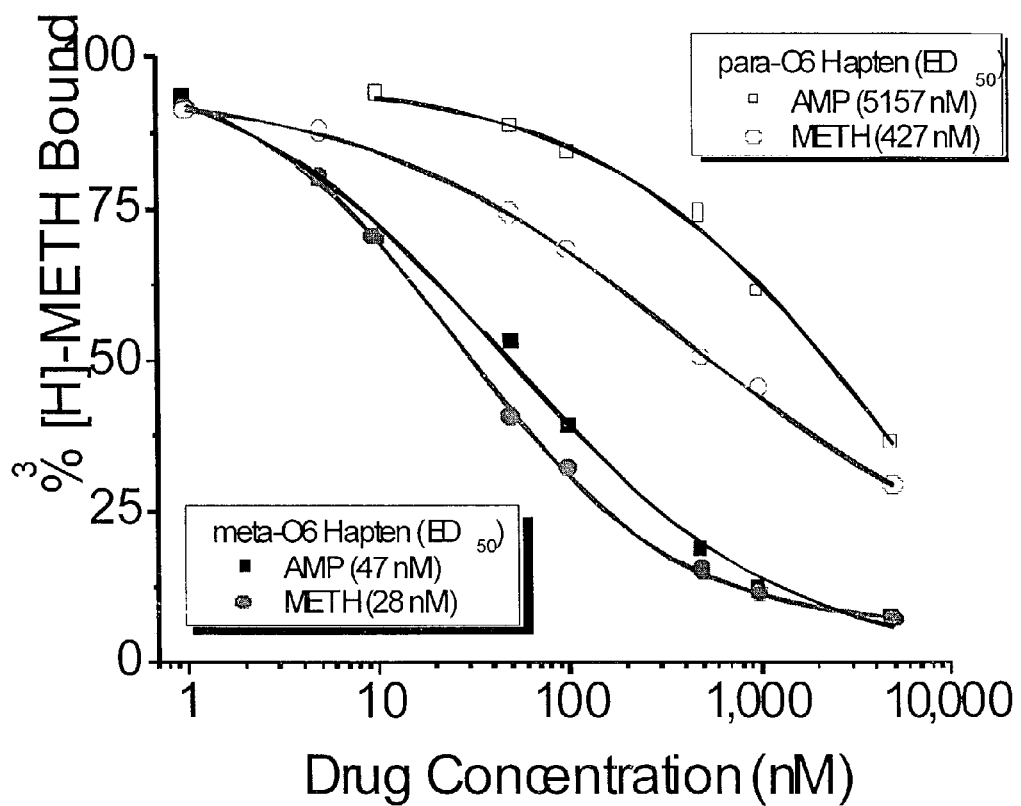
FIG. 7 shows radioimmunoassay cross-reactivity studies. The right two dose response curves show antiserum generated from immunization of two different rabbits with a para-O,6 d-methamphetamine hapten (hapten 10 in FIG. 4A with X=5 and connected at the 4 position). The left two dose response curves show antiserum generated from immunization with a meta-O,6 d-methamphetamine hapten (hapten 10 in FIG. 4A with X=5 and connected at the 3 position). The inhibition of [$^3$H]-methamphetamine binding for both antiserum was tested using both d-amphetamine and d-methamphetamine. These data shows that careful hapten design can leads to antiserum that has significant cross-reactivity with both d-amphetamine and d-methamphetamine.

Results from these studies show that the antiserum generated from the para-O,6 hapten (right two dose-response curves, FIG. 7) is significantly more specific for d-methamphetamine ($ED_{50}$=427 nM) than it is for d-amphetamine ($ED_{50}$=5157 nM). Indeed the relative cross reactivity for d-amphetamine is only 8.3% (427 nM/5157 nM×100%) of the value for d-methamphetamine. Thus, while this hapten might be useful in developing a highly specific assay for detection of d-methamphetamine, it would not be useful in generating a monoclonal antibody-based medication with high affinity and broad recognition for d-amphetamine like drugs.

In contrast, results from the radioimmunoassay analysis of the meta-O,6 antiserum (left two dose-response curves, FIG. 7) showed d-amphetamine ($ED_{50}$=47 nM) cross-reactivity is 59.6% (28 nM/47 nM×100%) of the value for d-methamphetamine ($ED_{50}$=28 nM). In these studies the meta-O,6 hapten also generated higher affinity antiserum than the para-O,6 hapten, as determined from the significantly lower $ED_{50}$ values for both d-amphetamine and d-methamphetamine. As an object of this invention is to generate a widely cross-reacting antiserum for d-amphetamine-like drugs, these data show the importance and uniqueness of the hapten design.

EXAMPLE 9

Comparison of Active and Passive Immunization as Treatments for D-Methamphetamine Addiction A series of male Sprague-Dawley rats are immunized with a d-methamphetamine-like hapten until high titers are achieved, or treated with anti-d-methamphetamine MAb. The rats are then repeatedly challenged with i.v. d-methamphetamine over several weeks. The ability of the antibodies to antagonize drug effects over an extended time period is assessed by behavioral measurements of response and using d-methamphetamine dose-response curves with dosing schedules that are designed to simulate repeated binge use of the drug. The rats for all of these studies are purchased with indwelling jugular venous catheters for i.v. administration of d-methamphetamine and anti-d-methamphetamine MAb.

For active immunization, one group of rats (n=6 for all groups) is immunized over a six week period prior to the start of the studies. An example immunization plan is 100 μg of the BSA-d-methamphetamine, emulsified in an equal volume of Titer-Max as adjuvant, followed at weeks 3 and 6 by a booster immunization. Ten days after the last boost, the anti-d-methamphetamine serum titers are checked in an ELISA. If the titers are elevated, behavioral testing begins on day 10–14 after the last boost.

For passive immunization, another group of rats is treated with 400 mg dose of monoclonal antibody the day before the start of the study. This dose of anti-d-methamphetamine monoclonal antibody (400 mg) should have the capacity to bind up to 2.1 mg/kg of d-methamphetamine on day 1 of the behavioral experiments, and up to 0.52 mg/kg of d-methamphetamine on day 16 (the final day of testing). A 2.1 mg/kg dose of d-methamphetamine in the rat would be about equivalent to a 150 mg binge use of d-methamphetamine in an average size human (i.e., about 150 lbs). The calculation of the d-methamphetamine (M.W. 149 g/mol) mol-eq dose of IgG assumes a 350 g rat, two IgG binding sites, a mass of 150,000 kDa, an in vivo first-order monoexponential loss of the IgG, and an IgG $t_{1/2}$ of 8.1 days (Bazin-Redureau et al., 1997).

The effectiveness of each therapy is measured by accessing the cumulative behavioral effects after administration of a range of d-methamphetamine doses over a 3 hr time period. This d-methamphetamine dosing strategy is used to simulate binge drug use and an addict's attempt to surmount the blocking effects of the antagonist by self-administration of progressively higher doses. The i.v. doses of 0.1, 0.3 and 1.0 mg/kg are administered at 0, 1.5 hrs and 3.0 hrs, respectively. This simulated binge dosing is repeated every 4 days (day 1, 4, 8, 12 and 16) for up to 16 days.

The EthoVision system, which has video tracking and digitized motion analysis, is used for continuous behavioral monitoring. d-methamphetamine-induced locomotor activity, e.g., distance traveled, percentage of the time spent moving, and animal rearing, are measured over a 6 hr period. From each day of behavioral experiments, the time to maximum effects after each dose of d-methamphetamine, the maximum effect, the area under the behavioral effect curve from the time of dosing to the end of each type of behavioral effect, and the duration of effects are calculated. The end of each behavioral effect is based on a statistical analysis of the average baseline response prior to drug administration. For instance, the point at which the animals' response has returned to 1+S.D. of the mean pre-drug response for two consecutive 2 min intervals. The data are analyzed by a two-way (dose of d-methamphetamine and time) repeated measures ANOVA, followed by a Student-Newman-Keuls post hoc test. The results are considered significant at $P<0.05$.

EXAMPLE 10

Pharmacodynamic Mechanisms of Monoclonal Antibody-Based Antagonism of High Dose (+)-Methamphetamine in Rats This example demonstrates that anti-(+)-methamphetamine monoclonal antibodies antagonize (+)-methamphetamine-induced locomotor effects by altering brain distribution of (+)-methamphetamine.

Two (+)-methamphetamine-like haptens with either a six- or four-carbon spacer group were used for antibody production. The complete synthesis of the (+)-P6-METH hapten (S-(+)-4-(5-carboxypentyl)methamphetamine HCl) was previously described (Byrnes-Blake et al., 2001). The (+)-P4-METH hapten (S-(+)-4-(3-carboxypropyl)methamphetamine HCl) was synthesized in a similar fashion. Both haptens were conjugated (Davis and Preston, 1981) to bovine serum albumin (BSA) for use as an antigen.

Female BALB/c mice (Charles River Laboratories, Wilmington, Mass.) were immunized with 100 ug of the hapten-conjugates emulsified 1:1 (v/v) with TiterMax adjuvant and boosted every 4 weeks with 50 ug of the antigen. Initial immunization and subsequent boosts were administered in two 40 ul subcutaneous injections. Blood samples were taken periodically by tail bleed to measure anti-(+)-methamphetamine antibody titer by an ELISA utilizing hapten-ovalbumin conjugates. Mice with the highest anti-(+)-methamphetamine serum titer was chosen for mAb production. Standard hybridoma technology was utilized for the production of the mAb. Hybridoma cell lines were screened for anti-(+)-methamphetamine antibody production by ELISA.

A low-affinity mAb (mAb 6H8; $K_d$=250 nM) was generated from immunization with the (+)-P4-METH-BSA conjugate, and a higher-affinity mAb (mAb 6H4; $K_d$=11 nM) was generated from immunization with the (+)-P6-METH-BSA conjugate. Both antibodies were IgG$_1$ with a κ light chain.

Figure 8:
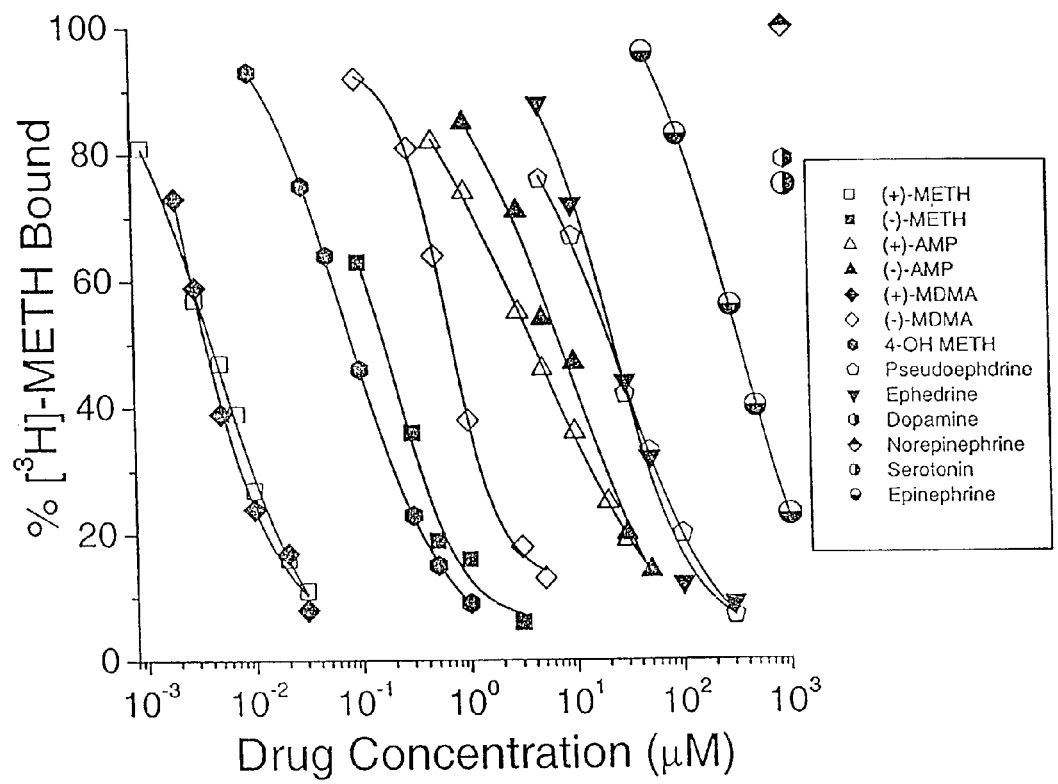
FIG. 8 shows the cross-reactivity profile of mAb 6H4 determined by radioimmunoassay similar to that described by Owens et al. (1988). The percentage bound equals the percentage of $B_0$ (amount of $^3$H-(+)-methamphetamine binding in the absence of any competing unlabeled drug) corrected for nonspecific binding. The data were fit with the use of sigmoidal curves that allowed the determination of the $IC_{50}$ values (concentrations of unlabeled drug that caused a 50% inhibition of $^3H$-(+)-methamphetamine binding).

The mAbs were highly specific for (+)-methamphetamine, having <0.1% cross-reactivity with most compounds tested. The one exception was the drug of abuse MDMA or "ecstasy" to which mAb 6H4 bound with a slightly higher relative affinity than (+)-methamphetamine (9 nM vs. 11 nM) (FIG. 8). Both mAbs were also stereospecific, having an approximately 50–200 times higher relative affinity for (+)-methamphetamine and (+)-amphetamine than for the minus forms of these drugs. In addition to the compounds shown in FIG. 8, there was no significant cross-reactivity with (+)- and (−)-MDA, (+)-norpseudoephedrine, L-phenylephrine, (+)-phenylpropanolamine, β-phenylethylamine and tyramine.

The day before being administered to the animals, the mAbs were ultracentrifuged at 100,000 g for 90 min at 4° C. and at 3,300 g for 20 min. This step was used to eliminate large-molecular-weight antibody complexes which can be highly antigenic. The mAb formulations were warmed to 37° C. before i.v. administration to the animals.

Locomotor Activity in the Rat Model

Locomotor activity was used as a measure of (+)-methamphetamine's effects because 0.3–3.0-mg/kg doses of (+)-methamphetamine produced dose-dependent and reproducible increases in both distance traveled and rearing (Rivière et al., 1999). Higher doses were not used because preliminary studies showed i.v. doses ≧5.2 mg/kg led to self-mutilation, and 10-mg/kg doses were sometimes lethal. The time of mAb treatment (t=30 min) was chosen because (+)-amphetamine formation is near maximum, (+)-methamphetamine distribution to the peripheral tissues is virtually complete (Rivière et al., 1999, 2000), and the drug-induced locomotor effects are profound at this time point.

Figure 9:
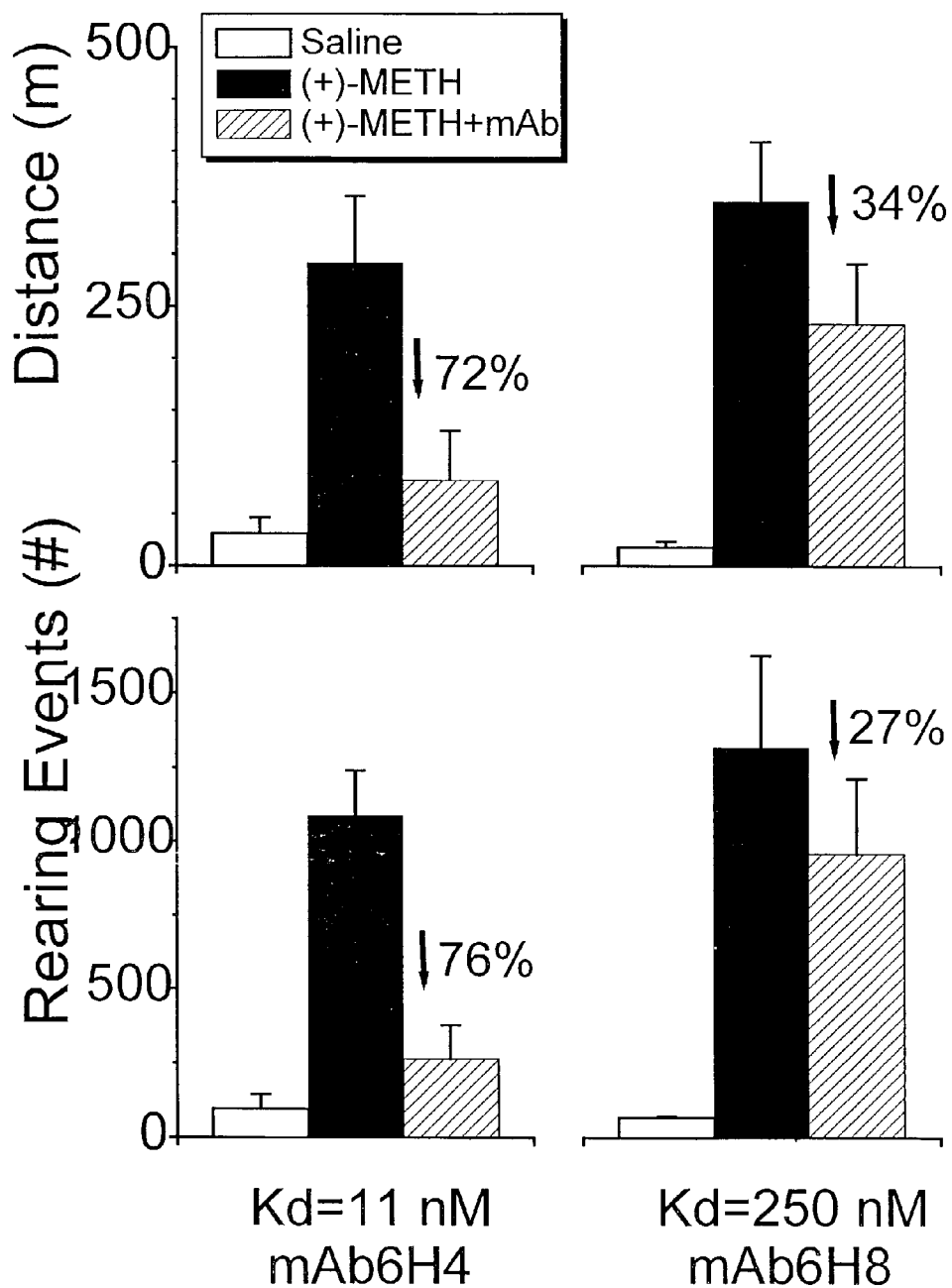
FIG. 9 compares the ability of a high (left panel) and a low affinity (right panel) mAb to reverse (+)-methamphetamine-induced stimulant effects (distance traveled and rearing behavior). Before the mAb experiments, the rats were treated on two separate days with a 1-mg/kg i.v. dose of (+)-methamphetamine followed 30 min later by buffer to establish control values (data not shown). For the mAb experiments, rats received another 1-mg/kg i.v. (+)-methamphetamine dose followed 30 min later by a high-affinity mAb or a low-affinity mAb. The data are shown as the mean +1 S.D. (n=6 per group). The arrows and percentages reflect the degree of mAb-induced reduction in (+)-methamphetamine behavioral response compared to control values.

Comparison of the Reversal of (+)-Methamphetamine-induced Locomotor Activity by a Low- and High-affinity Anti-(+)-Methamphetamine MAb To help elucidate the role of antibody affinity as a determinant of therapeutic efficacy, the low-affinity mAb (mAb 6H8) and the high-affinity mAb (mAb 6H4) were compared for their ability to reverse the locomotor activity following a 1-mg/kg i.v. (+)-methamphetamine dose. The high-affinity mAb more effectively antagonized both distance traveled and rearing than the low-affinity mAb (FIG. 9).

Figure 10:
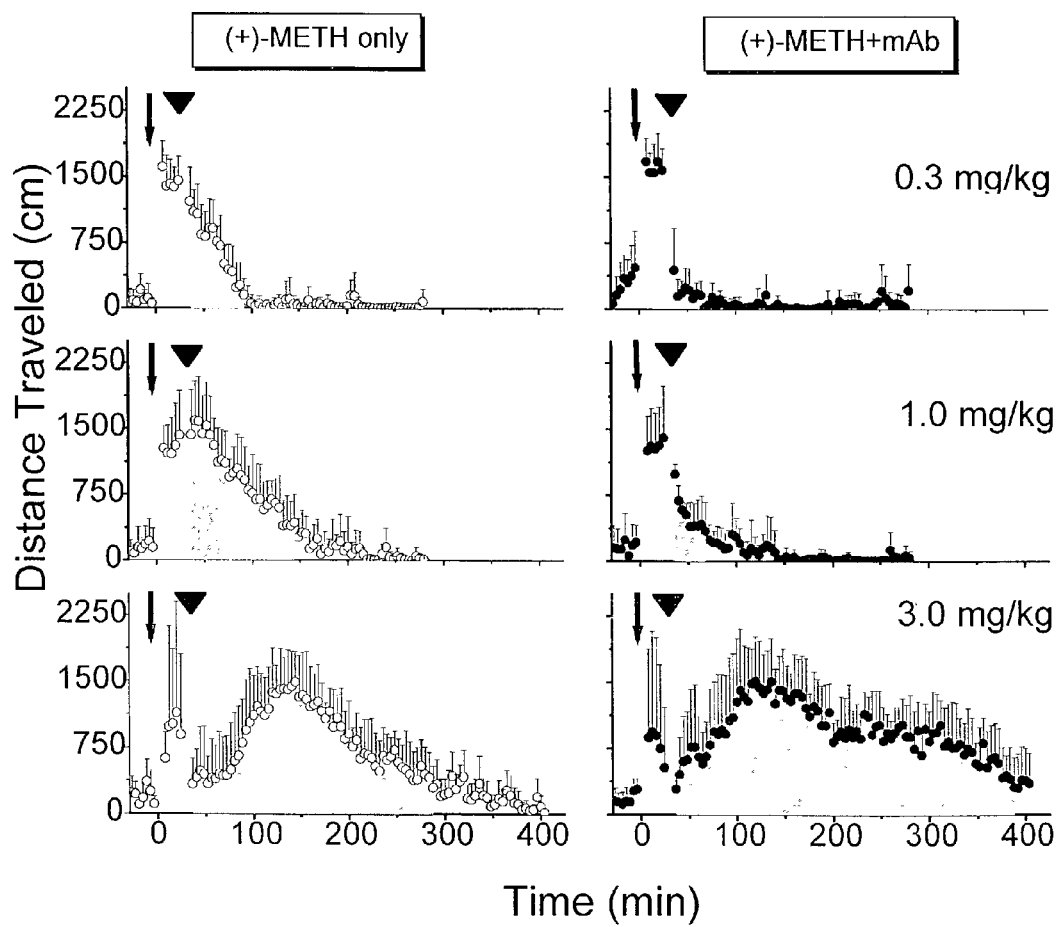
FIG. 10 shows the time course of (+)-methamphetamine-induced distance traveled in rats (n=6) with either buffer (left panel; open circles) or mAb6H4 (right panel; filled circles) treatment. The i.v. (+)-methamphetamine doses were 0.3, 1.0, and 3.0 mg/kg. The left arrow indicates the time of (+)-methamphetamine administration, and the arrowhead indicates the time of mAb6H4 administration. Shading indicates the duration of drug action above saline-induced (baseline) locomotor activity following buffer or mAb administration. The time needed to return to baseline was determined by statistical comparison of the behavior starting at t=30 min (time of treatment) with each animal's predosing behavior from −30 min to t=0.
Figure 11:
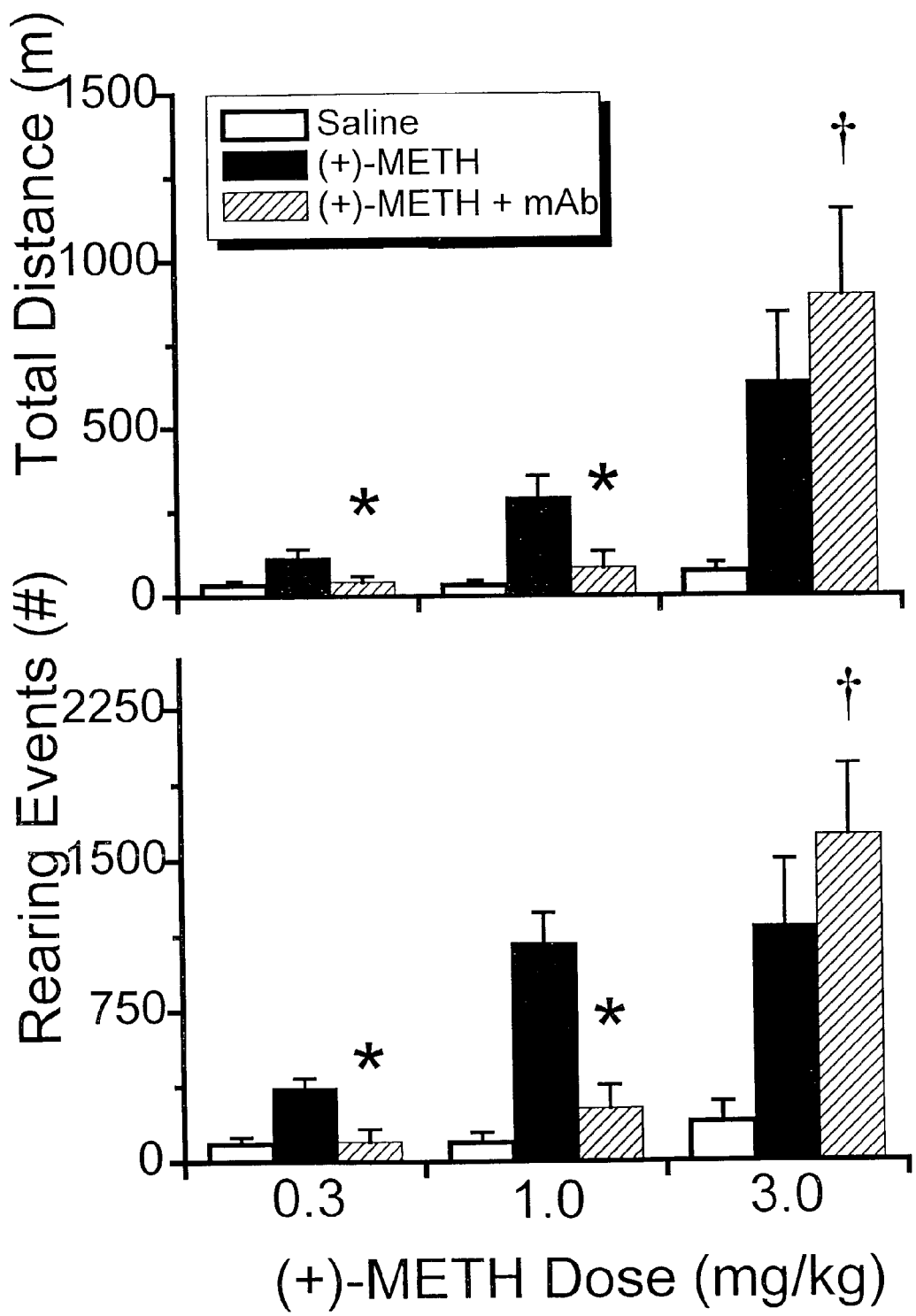
FIG. 11 shows the summary of dose-response results in groups of animals receiving 0.3, 1.0, or 3.0 mg/kg (+)-methamphetamine. The animals received saline followed 30 min later by buffer. Three days later, they received a priming dose (0.3, 1.0, or 3.0 mg/kg) of (+)-methamphetamine followed 30 min later by buffer (data not shown). This was followed 3 days later by a second (+)-methamphetamine priming dose with buffer at t=30 min. Three days later, they received a final (+)-methamphetamine dose (0.3, 1.0, or 3.0 mg/kg) followed at t=30 min by mAb6H4 (the high-affinity mAb). These data are shown as the means +1 S.D. (n=6 per group). * indicates a significant decrease in locomotor activity compared with (+)-methamphetamine; † indicates a significant increase in locomotor activity compared with (+)-methamphetamine ($p<0.05$).

Effect of the High-affinity Anti-(+)-Methamphetamine MAb on (+)-Methamphetamine-Induced Locomotor Activity These results show the ability of a fixed mAb dose to antagonize the effects of (+)-methamphetamine at three different doses. The time-dependent pattern of time spent moving was very similar to the time-dependent pattern of distance traveled, but it appeared to be a less sensitive measure. Therefore, the results for this parameter were not reported. FIG. 10 shows the time course of both distance traveled and rearing events after (+)-methamphetamine administration both without and with mAb treatment. FIG. 11 shows a summary of the total distance traveled and rearing events during the entire experimental period for each dosing group.

For both the 0.3 and 1.0 mg/kg (+)-methamphetamine doses, the high-affinity mAb substantially reduced the locomotor activities (distance traveled and rearing events) from baseline (+)-methamphetamine activities by >60% and >70%, respectively (all $p<0.05$). However, there was a significant increase in both distance traveled and rearing behavior when animals received 3.0 mg/kg (+)-methamphetamine followed by the mAb ($p<0.05$; FIG. 11).

At the end of the experimental protocol, animals that received the 1.0-mg/kg doses of (+)-methamphetamine also received a second saline treatment followed by buffer. The saline-induced behavior was not significantly different from that obtained at the start of the study ($p<0.05$; data not shown).

In addition to assessing mAb-induced changes in total distance traveled and the number of rearing events, changes in the duration of (+)-methamphetamine's action were also evaluated to measure the effects of mAb6H4. The duration of (+)-methamphetamine-induced locomotor effects following treatment (treatment=buffer vs. mAb) was approximately 1 h compared with 6 min for the 0.3-mg/kg dose and 2 h compared with 32 min for the 1.0-mg/kg dose. When the mAb was administered to the 3.0-mg/kg group, however, the duration of drug action increased from 4 to 6 h (FIG. 10).

Figure 12:
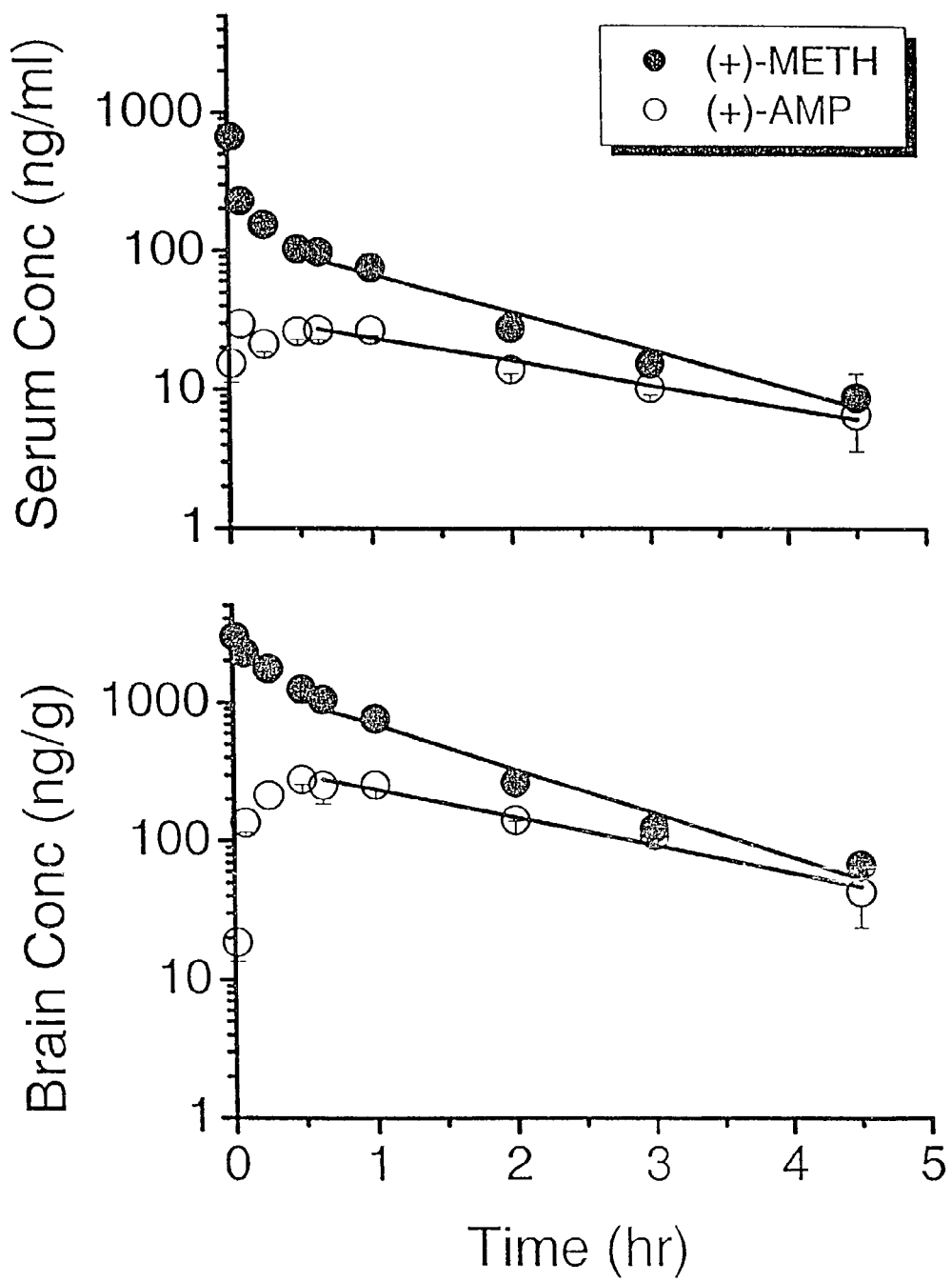
FIG. 12 shows average concentration-versus-time profiles for (+)-methamphetamine and (+)-amphetamine in serum (top panel) and brain (lower panel). The solid lines associated with the (+)-methamphetamine and (+)-amphetamine data show the linear-regression fit to the terminal log concentration-versus-time data as determined by model-independent analysis. All values are represented as the mean ±1 S.D. (n=3 per time point).

(+)-Methamphetamine and (+)-Amphetamine Pharmacokinetic Profile after (+)-Methamphetamine Administration The disposition of (+)-methamphetamine and its active metabolite, (+)-amphetamine, after a 1.0-mg/kg i.v. (+)-methamphetamine dose were similar to those of Rivière et al. (2000). The concentration-versus-time profiles of (+)-methamphetamine in serum and brain were best described by a two-compartment model with $1/y^2$ weighting. The distribution half-life of (+)-methamphetamine was 1.7 min in serum and 26 min for brain. In both serum and brain, the highest (+)-methamphetamine concentrations were achieved at the earliest measured time point (1 min; FIG. 12), followed by a biexponential decline. The metabolite (+)-amphetamine achieved apparent maximum concentrations in serum and brain at about 30 min (FIG. 12). Table 2 summarizes the pharmacokinetic values.

Figure 13:
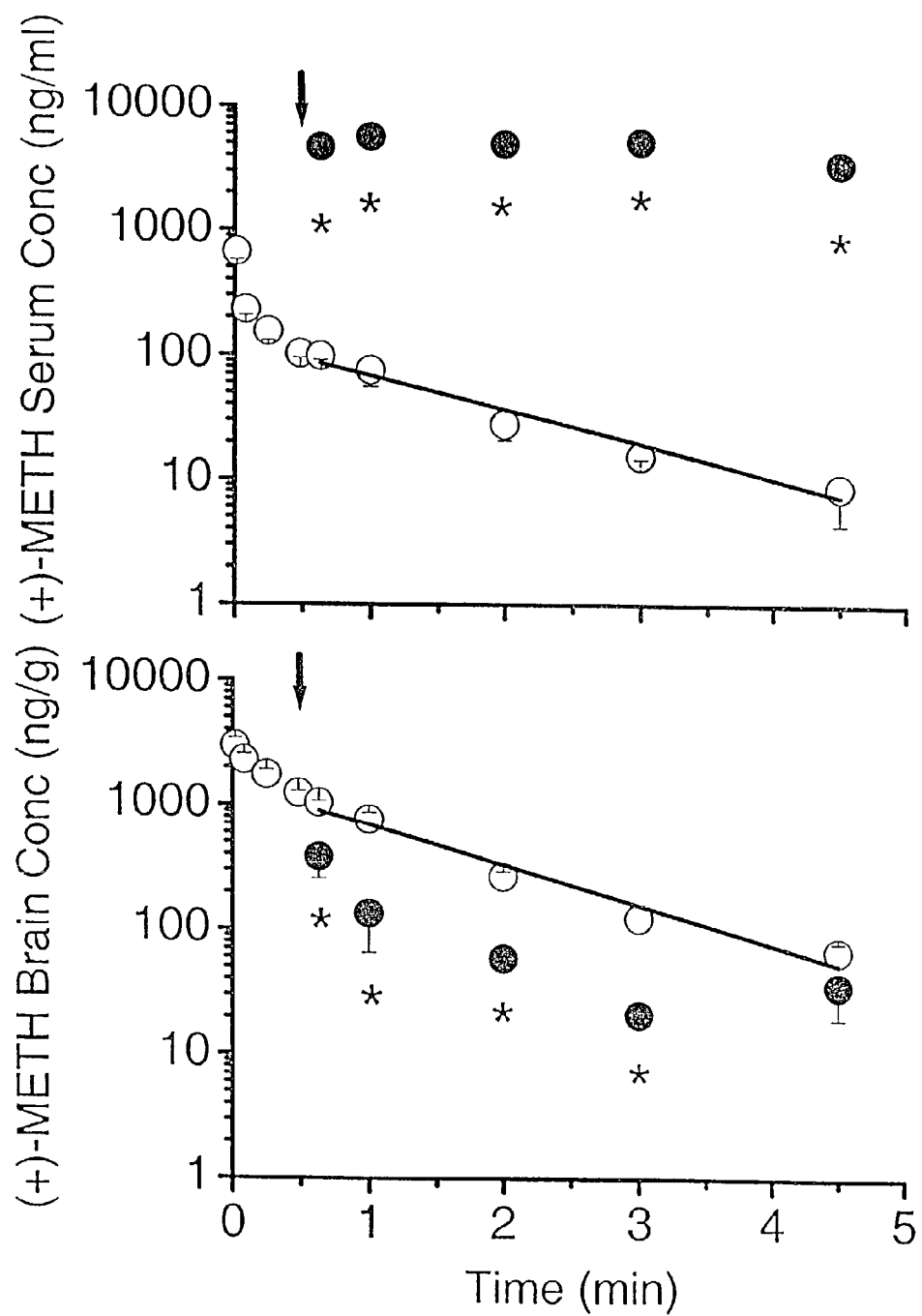
FIG. 13 shows average concentration-versus-time profiles for (+)-methamphetamine with (filled circle) and without (open circle) mAb6H4 administered at t=30 min in serum (top panel) and brain (lower panel). The solid lines associated with the data show the linear-regression fit to the terminal log concentration-versus-time data as determined by model-independent analysis. The arrow indicates the time of mAb administration. All values are represented as the mean ±1 S.D, n=3 per time point. * indicates a significant difference from control ($p<0.05$).
Figure 14:
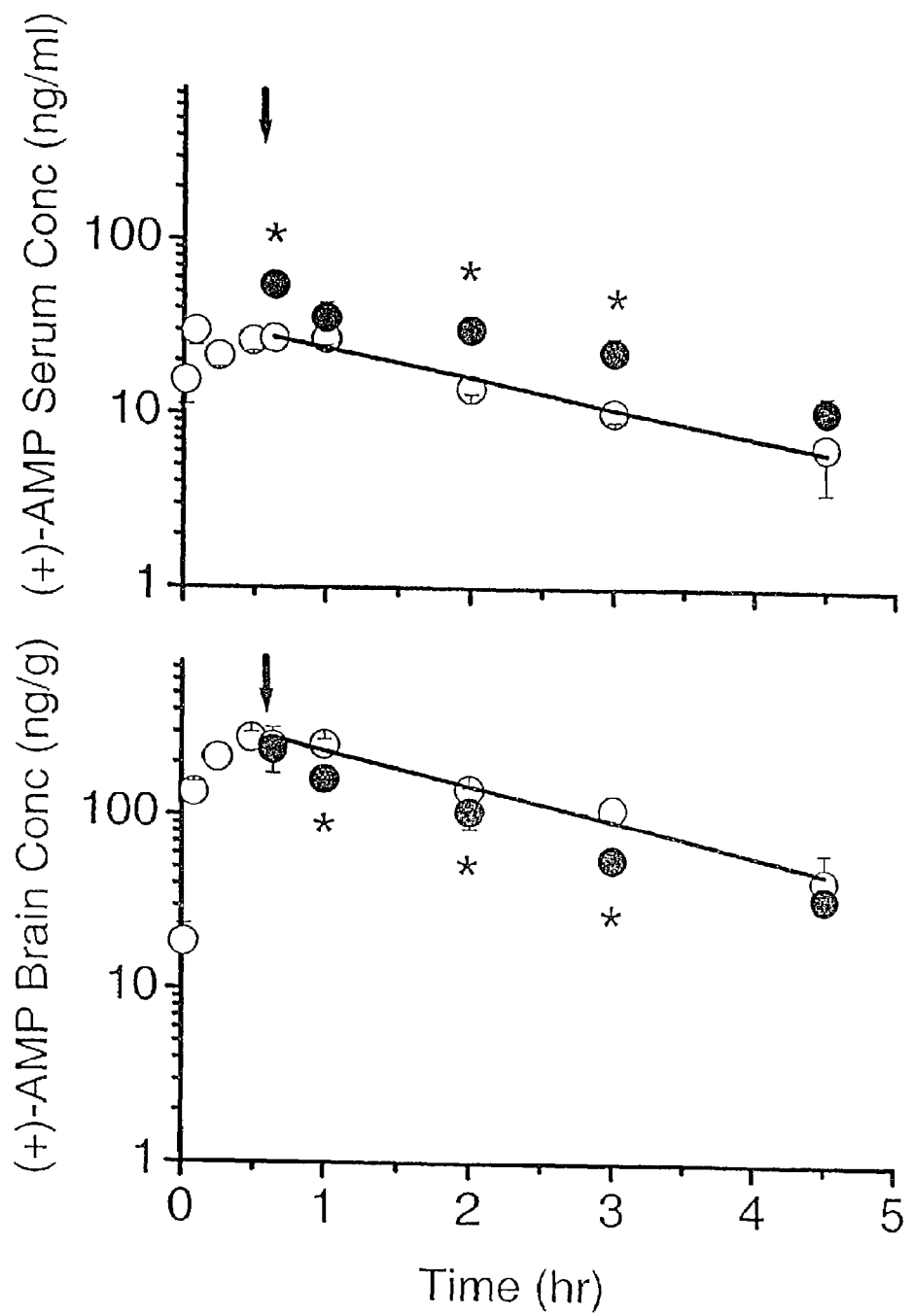
FIG. 14 shows average concentration-versus-time profiles for (+)-amphetamine with (filled circles) and without (open circles) mAb6H4 administration at t=30 min in serum (top panel) and brain (lower panel). The solid lines associated with the data show the linear-regression fit to the terminal log concentration-versus-time data as determined by model-independent analysis. The arrow indicates the time of mAb administration. All values are represented as the mean ±1 S.D. (n=3 per time point). * indicates a significant difference from control ($p<0.05$).

Effect of High-affinity Anti-(+)-Methamphetamine MAb on The Pharmacokinetic Profiles of (+)-Methamphetamine and (+)-Amphetamine Administration of the high-affinity mAb at $t=30$ min after (+)-methamphetamine administration led to a substantial change in the drug's disposition. Concentrations of (+)-methamphetamine in serum were significantly higher, corresponding to lower concentrations in brain (FIG. 13). The $AUC_{38min}^{4.5h}$ value for the serum (+)-methamphetamine concentration-versus-time profile showed a >9000% increase, whereas the $AUC_{38min}^{4.5h}$ for brain showed a >70% decrease. The $t_{1/2\lambda Z}$ values in the mAb-treated animals were not determined, as the elimination phase of the concentration-time profile could not be fully characterized within the 4.5-h experiment. The (+)-methamphetamine $AUC_{brain}$-to-$AUC_{serum}$ ratio was greatly decreased due to the large increase in serum concentrations (Table 1). The mAb had a significant effect on serum and brain (+)-amphetamine concentrations at some of the time points, but the effect was not as large as that seen with (+)-methamphetamine (FIG. 14). Because of the mAb's differential effects on (+)-methamphetamine and its metabolite (+)-amphetamine, there were major changes in the molar ratio of $AUC_{AMP}$ to $AUC_{METH}$ in both serum and brain (Table 1).

TABLE 2

Pharmacokinetic Parameters Of (+)-METH And Its Metabolite (+)-AMP After A 1-mg/kg i.v. (+)-METH Dose[a]

| Tissue | Drug | $t_{1/2 \lambda Z}$ | | $AUC_{38 min}^{4.5 h}$ | | $AUC_{brain}:AUC_{serum}$ | | Molar Ratio of (+)-AMP to (+)-METH AUC[b] | |
|---|---|---|---|---|---|---|---|---|---|
| | | Control | Treated | Control | Treated | Control | Treated | Control | Treated |
| | | h | | ng · h/ml or ng · h/g | | | | | |
| Serum | (+)-METH | 1.08 | NC | 123 | 12,266 | 1 | 1 | 0.49 | 0.01 |
| | (+)-AMP | 1.8 | NC | 55 | 73 | 1 | 1 | | |
| Brain | (+)-METH | 0.95 | NC | 1182 | 246 | 9.6 | 0.02 | 0.49 | 1.26 |
| | (+)-AMP | 1.5 | NC | 530 | 284 | 9.6 | 3.4 | | |

[a]Data are shown from animals both without treatment (control) and with treatment (1-mol equivalent dose of mAb). All parameters were calculated by model-independent analysis. NC, not calculated due to inadequate sampling during the terminal phase.
[b]The molar ratio of (+)-AMP to (+)-METH AUC was calculated by dividing the nmol · h/g or nmol · h/ml AUC values.

Discussion

The overall goal of these studies was to determine the mechanisms associated with anti-(+)-methamphetamine mAb-based antagonism of (+)-methamphetamine-induced locomotor effects in a rat overdose model. The influence of mAb affinity on therapeutic success was first examined because there was no previous studies addressing this important issue. Two mAbs were developed for these studies. Both mAbs were of the same isotype and light chain and were highly specific for (+)-methamphetamine. They differed in only one important aspect: a 25-fold difference in $K_d$ values.

The higher-affinity mAb was two to three times more effective than the lower-affinity mAb at reducing (+)-methamphetamine-induced distance traveled and rearing events (FIG. 10). However, even the higher-affinity mAb6H4 did not achieve the maximum possible antagonism against the effects of (+)-methamphetamine, and experimental evidence suggests that another 10- to 25-fold increase in mAb affinity would be needed to significantly improve the therapy further. The hypothesis that a higher affinity mAb (e.g., $K_d=1$ nM) would offer substantial improvements is supported by other studies showing that an anti-phencyclidine mAb with a $K_d$ of 1.8 nM can completely reverse phencyclidine's locomotor effects (Hardin et al., 1998). A single dose of that antibody can reduce brain concentrations of phencyclidine for at least one month (Proksch et al., 2000). However, it should be noted that the (+)-methamphetamine rat model is complicated by the presence of a pharmacologically active metabolite, (+)-amphetamine, with which mAb6H8 and mAb6H4 do not cross-react. A mAb with increased cross-reactivity for (+)-amphetamine (or a cocktail of an anti-(+)-methamphetamine and an anti-(+)-amphetamine mAb) may improve the effectiveness of the therapy.

Due to its relatively superior effectiveness, the high-affinity mAb was used for all subsequent behavioral and pharmacokinetic studies. A fixed dose of the high-affinity mAb (equimolar to the (+)-methamphetamine body burden at 30 min after a 1-mg/kg (+)-methamphetamine dose) effectively antagonized (+)-methamphetamine-induced effects when the (+)-methamphetamine dose was equal to or less than the mAb dose (FIGS. 10 and 11). The mAb also significantly decreased the drug's duration of action at both (+)-methamphetamine doses (FIG. 10). However, when the drug dose was greater than the mAb binding capacity (i.e., at the 3.0-mg/kg), locomotor activity was increased after mAb administration compared with that seen after (+)-methamphetamine administration followed by buffer.

Several possible explanations exist for these apparent complex changes in behavior at the high (+)-methamphetamine-to-mAb ratio. First, the locomotor activity could have maximized at doses somewhere between 1 and 3 mg/kg. This is described as a so-called inverted-U-shaped dose-response curve. If this were the case, mAb administered at a dose equimolar to a 1-mg/kg (+)-methamphetamine dose could have neutralized part of the drug dose, thus shifting the dose-response curve back to the point of an apparent increase in locomotor activity. This hypothesis was tested by quantitating locomotor activity in rats after administering a 1.8-mg/kg (+)-methamphetamine dose (a half log dose between 1- and 3-mg/kg). The 1.8-mg/kg dose produced locomotor effects that were about equal to the effects of the 1- and 3-mg/kg (+)-methamphetamine doses (data not shown). Thus, the increased activity following mAb treatment in the 3.0-mg/kg-dose group could not be explained by a simple shift to the left in the (+)-methamphetamine dose-response curve.

A possible pharmacodynamic reason for the increase in the behavior is described as follows. It is quite likely that (+)-methamphetamine's multiple mechanisms of action in the brain and peripheral sites have different concentration-response relationships and are more or less susceptible to the neutralizing, beneficial effects of the mAb. Thus, when the mAb is present in limited amounts relative to the amount of drug, the mAb would presumably have the greatest effects on the most accessible and lowest-affinity effector sites. It is also possible that the mAb could preferentially neutralize the behaviorally suppressive effects, like stereotyped behavior, while allowing the stimulatory effects to predominate.

There are also pharmacokinetic and immunological explanations for the increase in total locomotor activity. Firstly, the mAb appeared to have substantially slowed (+)-methamphetamine's entry into the CNS through high-affinity binding in serum (FIG. 13). This would have led to a decreased amount of (+)-methamphetamine reaching the CNS but prolonged availability of the drug. Secondly, significant amounts of the active metabolite, (+)-amphetamine, may have accumulated because (+)-amphetamine has a longer half-life than (+)-methamphetamine in rats (Rivière et al., 1999, 2000; Cho et al., 2001; Table 2). In addition, (+)-amphetamine does not significantly cross-react with the mAb. Thirdly, the association and dissociation of (+)-methamphetamine with the mAb and its relationship to the influx and efflux of the drug in the CNS could also be factors. In an attempt to address this point, the behavioral effects following a 3-mg/kg intraperitoneal (i.p.) (+)-methamphetamine dose were compared with those of the 3-mg/kg i.v. dose. The i.p. route was chosen because it provides a model of a slower drug input into the brain and would produce greater (+)-amphetamine concentrations due to liver first-pass metabolism. The data showed that the i.p. route of administration resulted in significantly increased effects compared with those of the i.v. route. These findings suggest that the rate of drug entry in the CNS and the increased (+)-amphetamine concentrations are important factors in (+)-methamphetamine-induced locomotor activity and the effectiveness of the mAb.

Pharmacokinetic studies were conducted to help determine some of the mechanisms for the behavioral effects. These studies were carried out with a 1:1 molar ratio of (+)-methamphetamine to mAb. Serum was chosen because (+)-methamphetamine is transported to its sites of action via the bloodstream and mAbs are confined mainly to the serum volume. The brain was chosen for study because it is the major site of action contributing to (+)-methamphetamine's locomotor effects.

Immediately after the administration of mAb6H4, serum (+)-methamphetamine concentrations dramatically increased and remained high throughout the duration of the experiment (FIG. 13). The concentrations were measured for only 4.5 h so that better understanding of the pharmacokinetic processes associated with the pharmacological-effect period of (+)-methamphetamine (FIG. 10) can be obtained. The mAb also produced immediate decreases in brain (+)-methamphetamine concentrations which were sustained for at least 3 h. This immediate reduction in brain concentrations was totally consistent with the immediate reversal of (+)-methamphetamine-induced locomotor effects at the 1-mg/kg dose (FIG. 10). However, by 4.5 h, the brain concentration appeared to rebound and was then not significantly different from that of the control animals. By this point, however, the (+)-methamphetamine concentration in control and treatment animals appeared to be below the threshold concentration leading to locomotor activity. These pharmacokinetic changes for (+)-methamphetamine are consistent with a similar dramatic decrease (and rebound) in phencyclidine brain concentrations after anti-phencyclidine Fab fragment treatment in rats (Valentine and Owens, 1996). It is believed that these changes resulted from the rapid mAb-induced redistribution of drug from the brain, followed by an increase in drug concentrations due to a slower redistribution from other tissues.

The effect of the mAb on (+)-amphetamine concentrations was small, compared to its effect on (+)-methamphetamine concentrations. This is not surprising because the mAb had little cross-reactivity with (+)-amphetamine in vitro. The small mAb-induced increase in serum concentrations of (+)-amphetamine may result from increased amounts of (+)-methamphetamine in the serum available for metabolism. This hypothesis can be proved by knowing the free concentrations and serum clearance of (+)-methamphetamine. The small decrease in (+)-amphetamine concentrations in brain and the dramatic decrease of (+)-methamphetamine concentrations in brain suggest the possibility of brain conversion of (+)-methamphetamine to (+)-amphetamine. However, data are insufficient to fully support this conclusion.

These data indicate that the 70% decrease in brain (+)-methamphetamine AUC is a direct cause of the 70% decrease in behavioral effects following mAb treatment at the 1-mg/kg dose. In addition, (+)-amphetamine formation does not play a significant role in (+)-methamphetamine's pharmacological effects at this dose. This would not be the case at the 3-mg/kg dose because brain (+)-amphetamine concentrations would be approximately threefold greater at all time points. The ratio of the (+)-amphetamine AUC to the (+)-methamphetamine AUC in serum and brain of rats is about 49% (Rivière et al., 2000). However, the amounts of (+)-amphetamine in humans appear to be substantially lower (Cook et al., 1993). Therefore, the prediction of beneficial effects in humans based on rat data is somewhat hindered by the very high (+)-amphetamine-to-(+)-methamphetamine ratio in the rat.

In conclusion, the effects of mAb therapy for (+)-methamphetamine are dependent on mAb affinity, dose and specificity. Monoclonal antibodies with improved affinity for (+)-methamphetamine, and possibly increased cross-reactivity with (+)-amphetamine, could offer improvements in the effectiveness of the therapy.

Experimental Protocols

Male Sprague-Dawley rats were obtained from Hilltop Laboratories (Scottsdale, Pa.) with an indwelling jugular venous catheter (Silastic medical-grade tubing, 0.020-inch inner diameter and 0.037-inch outer diameter; Dow Corning Corporation, Midland, Mich.). Catheter patency was maintained with a saline and 25 U of heparin flushes every other morning. The rats were housed separately, and their weight was maintained between 270–300 g throughout the experiment. All animal experiments were conducted with the approval of the Institutional Animal Care and Use Committee of the University of Arkansas for Medical Sciences and were in accordance with the *Guide for the Care and Use of Laboratory Animals* adopted and promulgated by the National Institutes of Health.

Protocol for (+)-Methamphetamine Locomotor Activity Studies

The parameters of distance traveled (in centimeters or meters), number of rearing events, and time spent moving (in seconds) were individually quantified for each animal. The general protocol was previously described (Hardin et al., 1998; Rivière et al., 1999). Briefly, animals were placed in polyethylene chambers that contained a bedding of dark-gray clay. Animal behavior was videotaped, and the video images were digitized and quantitated in 4-min intervals by EthoVision software (Noldus Information Technology Inc., Sterling, Va.). The duration of drug action was calculated for each parameter starting at 30 min (time of treatment) and until the locomotor activity returned to baseline. Locomotor activity was determined to have returned to baseline levels when two consecutive 4-min intervals were less than or equal to the mean +1 S.D. of the 30-min behavioral baseline observed just before drug administration.

Rats were habituated to the behavioral monitoring chambers before the start of the experimental protocol. This was accomplished by placing the rats in the chambers for a minimum of 3 h per day for 4–6 consecutive days. After the habituation phase, the rats were then randomly divided into three (+)-methamphetamine-dosing groups (n=6 rats per group). The rats in each group were dosed every three days for a total of 10 days. All saline and (+)-methamphetamine injections were administered via the jugular catheter as a 15-sec i.v. infusion.

On day 1, all groups received saline followed at 30 min by mAb buffer to obtain baseline (non-drug-induced) behavior. Then on days 4 and 7, they received a pretreatment dose of either 0.3, 1.0, or 3.0 mg/kg (+)-methamphetamine followed at 30 min by buffer. Two (+)-methamphetamine sessions were conducted because preliminary studies showed that, on average, the rats had a lower (+)-methamphetamine-induced locomotor response to the first i.v. injection of the drug than to the second and subsequent injections (data not shown). Thus, the second pretreatment drug dose was used to determine the (+)-methamphetamine-induced locomotor activity baseline.

The third and final dose of 0.3, 1.0, or 3.0 mg/kg (+)-methamphetamine was administered on the last day of the protocol. This dose was followed at t=30 min by i.v. injection of the high-affinity anti-(+)-methamphetamine mAb (mAb6H4; $K_d$=11 nM). The 30-min time point was chosen for treatment because previous studies showed that locomotor activity and active metabolite concentrations ((+)-amphetamine) in tissues are near maximum at 30 min (Rivière et al., 1999, 2000). The amount of mAb administered was 367 mg/kg, which is equimolar (assuming two binding sites per IgG molecule) to the amount of (+)-methamphetamine left in the body at t=30 min. The amount of drug remaining was determined from the serum pharmacokinetic data from Rivière et al. (1999) and by the equation: body burden=dose×$e^{-kt}$ (Rowland and Tozer, 1995). This simple monoexponential elimination phase equation could be used to calculate the body burden at 30 min because the distribution phase for (+)-methamphetamine in serum is extremely short ($t_{1/2dist}$=9 min).

All control buffer and mAb solutions were administered via the jugular venous catheter in an 8-ml volume at 2 ml/min. Three days after the end of the experimental protocol for the 1-mg/kg group, locomotor activity from a second saline administration was monitored to determine whether any changes had occurred in baseline activity.

In another study, the therapeutic effectiveness of the low-affinity mAb (mAb6H8; $K_d$=250 nM) and that of the high-affinity mAb were directly compared. Data from the 1-mg/kg group in the experiment described in the previous paragraphs (with mAb6H4) were compared with data from a group of rats (n=6) administered 1 mg/kg (+)-methamphetamine and treated at t=30 min with mAb6H8. All other aspects of the protocol were as just described.

Protocol for (+)-Methamphetamine and (+)-Amphetamine Pharmacokinetic Studies

Before each pharmacokinetic experiment, a 1-mg/kg (+)-methamphetamine dose plus a 333-μCi/kg $^3$H-(+)-methamphetamine dose was prepared in sterile saline. This allowed the administration of approximately 100 μCi per rat by injection of 1 μl/g of rat body weight.

Male Sprague-Dawley rats were randomly placed into two groups. The first group (n=3 per time point for all pharmacokinetics studies) was the control group that did not receive antibody. Rats in this group were administered a 15-sec i.v. injection of the (+)-methamphetamine/$^3$H-(+)-methamphetamine solution via the jugular venous catheter and were then placed in metabolism cages (Nalge Nunc International, Rochester, N.Y.). At various predetermined times after injection (1, 5, 15, 29, and 38 min; 1, 2, 3, and 4.5 h), the rats were sacrificed. At the early time points (1 and 5 min), the rats were anesthetized before drug injection so that an immediate laparotomy could be performed to obtain blood from the inferior vena cava, and decapitation could take place at the correct time. At later time points (15 min onward), rats were anesthetized 5 min before the desired time of sacrifice (decapitation) to allow time for obtaining sufficient depth of anesthesia and for the laparotomy and blood collection to take place. Ethyl ether was used for anesthesia so that hemodynamic stability could be maintained before animal sacrifice. Immediately after blood collection, the rats were decapitated and the brain w as removed. The brain was rinsed with saline, weighed, and placed in liquid nitrogen within 3 min of decapitation. Hematocrit values were obtained for each animal. The blood was allowed to clot and serum was obtained after centrifugation. The serum and brain tissues were stored at −80° C. until analyzed.

The second group was the mAb-treatment group. All aspects of the experiment were same as those described for the control group, with the following exception. At t=30 min, each rat was administered 367 mg/kg of the mAb (equimolar to the body burden of (+)-METH in the rat at 30 min). The mAb was given via the jugular venous catheter in an 8-ml volume at 2 ml/min. Because the experimental protocol was the same up until the mAb was administered, the time points before 30 min were not repeated in this group.

Analysis of Drug Concentrations (+)-methamphetamine and (+)-amphetamine were extracted from serum and brain with the use of a solid-phase extraction procedure. For serum analysis, 300 μl of guanidine HCl was added to 200-μl of each serum sample to denature the proteins. The samples were vortexed and placed on a gentle shaker for 30 min. Then, 120 μl of a solution containing 0.025-mg/ml (+)-methamphetamine/(+)-amphetamine internal standard were added, and each sample mixture was placed directly on solvent-conditioned Oasis HLB extraction cartridges (1 ml, 30 mg; Waters Corporation, Milford, Mass.). After sample application, the cartridges were centrifuged at 230 g for 1 min, washed with 1 ml of water, and then centrifuged. For elution of both (+)-methamphetamine and (+)-amphetamine, the cartridges were transferred to siliconized test tubes, 1 ml of methanol was added, and 1 min of centrifugation followed. Then, 1 ml of methanol:acetic acid (98:2) was added, followed by centrifugation.

To determine (+)-methamphetamine and (+)-amphetamine concentrations in the brain, tissues were homogenized for 30 sec in 5× (v/w; ml/g) ice-cold water with a tissue homogenizer (Tekmar Company, Cincinnati, Ohio). A 200-μl aliquot was then added to 300 μl of 8 M guanidine HCl. The mixture was vortexed and gently shaked for 30 min. Then, 500 μl of water, 120 μl of the (+)-methamphetamine/(+)-amphetamine internal standard, and 300 μl of a 10% $ZnSO_4$ solution (to precipitate proteins) were added. The mixture was vortexed, placed on ice for 5 min, and centrifuged at 12,500 g for 5 min.

Supernatants from the brain samples were applied to conditioned extraction cartridges and then centrifuged at 600 g for 4 min. The brain precipitates left over from the 12,500 g centrifugation were resuspended in 500 μl of water and centrifuged at 12,500 g for 3 min. The supernatants were then added to their respective extraction columns and centrifuged at 600 g for 4 min. This was followed by a 1-ml water wash, with another 4 min centrifugation at 600 g. Finally, the cartridges were placed in siliconized test tubes for sample collection. The elution process was as described for the serum samples.

After elution, the samples were taken to dryness over 3 h in a vacuum centrifuge (Savant Instruments, Inc., Farmingdale, N.Y.) with no heat or cryopumping. They were resuspended in 120 μl of 7% acetonitrile and 93% water (the HPLC starting conditions). A Waters Corporation HPLC system consisting of a pump controller, autoinjector, UV detector, Millennium software, and a Symmetry Shield RP18 (3.5 μm, 4.5×75 mm) column was used to separate (+)-methamphetamine and (+)-amphetamine for quantitation. The mobile phase was 7% acetonitrile and 93% water with 0.1% trifluoroacetic acid. Fractions (10 sec) were collected, and the $^3$H-(+)-methamphetamine and $^3$H-(+)-amphetamine containing fractions were quantified by liquid scintillation spectrometry. The serum and brain drug concentrations were determined from the ratio of unlabeled (+)-methamphetamine or (+)-amphetamine to radiolabeled tracer as previously described (Rivière et al., 1999).

Pharmacokinetic Analysis

Brain concentrations were corrected for residual blood content in the organ with the equation:

$$C_{Total} = \frac{C'_{Tissue} - (C_B * V_B)}{1 - V_B},$$

where $C_{Total}$ is the concentration of (+)-methamphetamine or (+)-amphetamine in the tissue corrected for blood concentration; $C'_{Tissue}$ is the tissue drug concentration before correction for blood content; $C_B$ is the drug concentration in the blood; and $V_B$ is the volume fraction of the residual blood in each tissue (Triplett et al., 1985). $V_B$ values for brain (0.037) were obtained from Khor et al. (1991).

When no mAb was present, the blood drug concentration was assumed to be equal to the serum drug concentration, as (+)-methamphetamine and (+)-amphetamine distribute equally in red blood cells and serum (Rivière et al., 2000). When the mAb was present, it was assumed (due to high-affinity mAb binding) that all of the drug was in the serum rather than in the red blood cells. The (+)-methamphetamine or (+)-amphetamine concentration in blood for this calculation was determined by multiplying each animal's serum drug concentration by 1 minus their respective hematocrits (Valentine and Owens, 1996).

To determine the distribution half-lives of (+)-methamphetamine and (+)-amphetamine, the average concentration-vs-time curves were analyzed by model-dependent methods using a nonlinear least-squares fitting routine. The data were fit to both two-and three-compartment i.v. bolus models, with y (predicted concentration), 1/y, or $1/y^2$ weighting. The best-fit line was chosen by visual inspection and analysis of the residuals. The terminal elimination half-life ($t_{1/2\lambda z}$) was determined, where possible, from the terminal phase of the average concentration-vs-time profiles for (+)-methamphetamine and (+)-amphetamine with the use of model-independent analysis. The area under the concentration time curve (AUC) for serum and brain were determined from t=38 min (immediately after mAb treatment) to 4.5 h (last measured time point). Because we could not accurately estimate the pharmacokinetic values after mAb ($t_{1/2\lambda z}$=8 days, Bazin-Redureau et al., 1997) administration due to the limited period of serum and brain sampling, $AUC_{38min}^{4\ 5h}$ values were used for comparative purposes. Nevertheless, sufficient data were collected for a comparison of pharmacodynamic changes during (+)-methamphetamine's pharmacological effect period. All pharmacokinetic analysis was performed with the use of WinNonlin V3.0 (Pharsight Corporation, Mountain View, Calif.).

Statistical Analysis

To determine if the administration of the high-affinity mAb affects (+)-methamphetamine-induced locomotor activity, the difference between the baseline (+)-methamphetamine activity (day 7) and (+)-methamphetamine activity after treatment (day 10) was calculated. These differences were then analyzed in a one-way ANOVA context with the dose level of (+)-methamphetamine as the factor. Student's t tests of the dose means were carried out, and p-values were adjusted with Holm's correction when applicable. These analyses were performed with SAS System V8.0 software (Cary, N.C.).

For the animals dosed with 1-mg/kg (+)-methamphetamine, comparisons between saline baseline activity (day 1) and a second saline-buffer treatment at the end of the protocol were tested with a paired Student's t-test. To assess mAb-induced changes in (+)-methamphetamine and (+)-amphetamine tissue concentrations at each time point, a Student's two-tailed t test was used. These analyses were conducted with SigmaStat V1.0 software (Jandel Scientific, San Rafael, Calif.). A significance level of p<0.05 was used for all statistical analyses.

EXAMPLE 11

Effects of Anti-Meth Fab on Meth-Induced Behavioral Effects

Figure 15A:
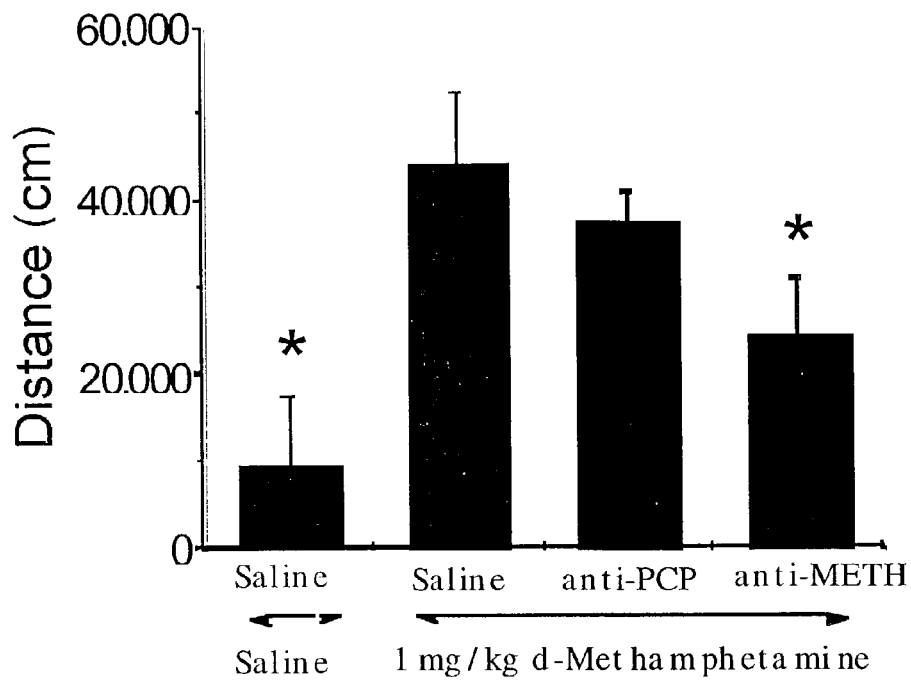
FIG. 15A shows the distance travel from 30 minutes after saline or d-methamphetamine administration until the end of the experiment, 4.5 hours later. *$p<0.05$ compared to a 1 mg/kg dose of methamphetamine followed by the saline control treatment. †$p<0.05$ compared to a 1 mg/kg dose of methamphetamine followed by the anti-methamphetamine Fab treatment.
Figure 15B:
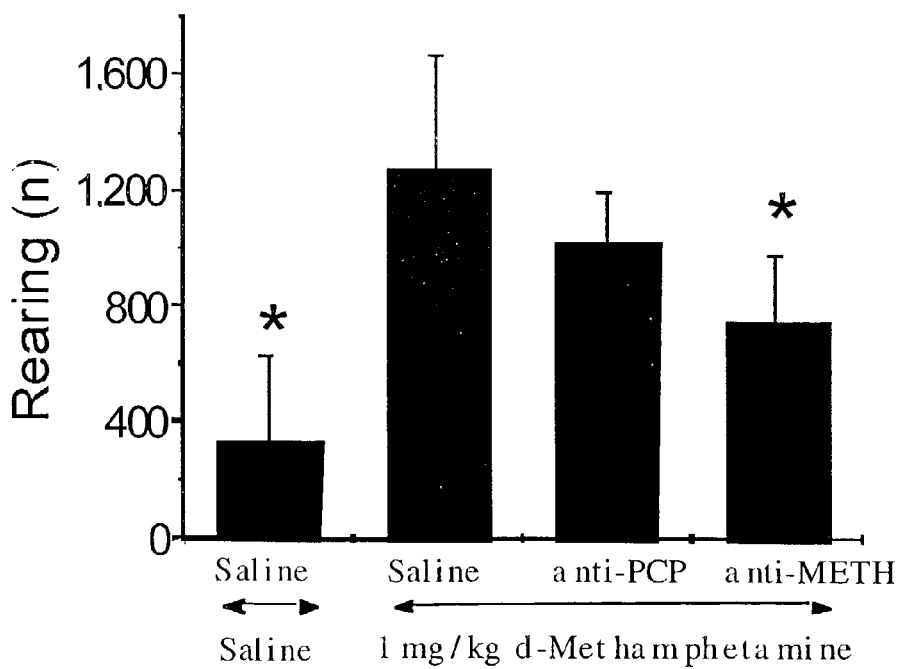
FIG. 15B shows the number of metampetamine-induced rearing events from 30 minutes after saline or d-methamphetamine administration until the end of the experiment, 4.5 hours later. At the 30 min the animals were treated with ether saline, anti-phencyclidine Fab or anti-d-methamphetamine Fab. *$p<0.05$ compared to a 1 mg/kg dose of methamphetamine followed by the saline control treatment.

Based on the distance traveled parameter, the duration of action of methamphetamine-induced effects following a 1 mg/kg iv dose was about two hours (116±17 min). After treatment with anti-PCP Fab the duration of activity was 111±10 min. After treatment with anti-methamphetamine Fab the duration of activity was 75±22 min. Both the distance traveled (FIG. 15A) and the number of rearing events (FIG. 15B) were significantly different from the behaviors produced by saline followed by methamphetamine administration (p<0.05). The anti-PCP Fab treatment produced some mild reductions in methamphetamine-induced locomotor activity, which were similar to the mild reductions in behavior we have found in other experiments in which polyclonal non-specific antibody is used to treat PCP-induced locomotor activity. As a percentage of the control saline treatment, the monoclonal anti-methamphetamine Fab produced a 55% decrease in the distance traveled (FIG. 15A). The number of rearing events (FIG. 15B) and the time spent moving (results not shown) were also decreased by 55% and 60%, respectively.

Since the monoclonal antibody used for these studies did not significantly bind to d-amphetamine (a psychoactive metabolite present at very high levels in the rat, but at significantly lower levels in the human) and it was a low affinity antibody (about 250 nM), the therapeutic potential for antibody based medications for overdose are quite significant. This is especially important since no therapies currently exist. With the use of improved hapten design and production of antibodies with significantly lower Kd values (e.g., <30 nM), this invention should provide a significant breakthrough in treatment of overdose due to d-methamphetamine-like drugs.

EXAMPLE 12

Figure 16:
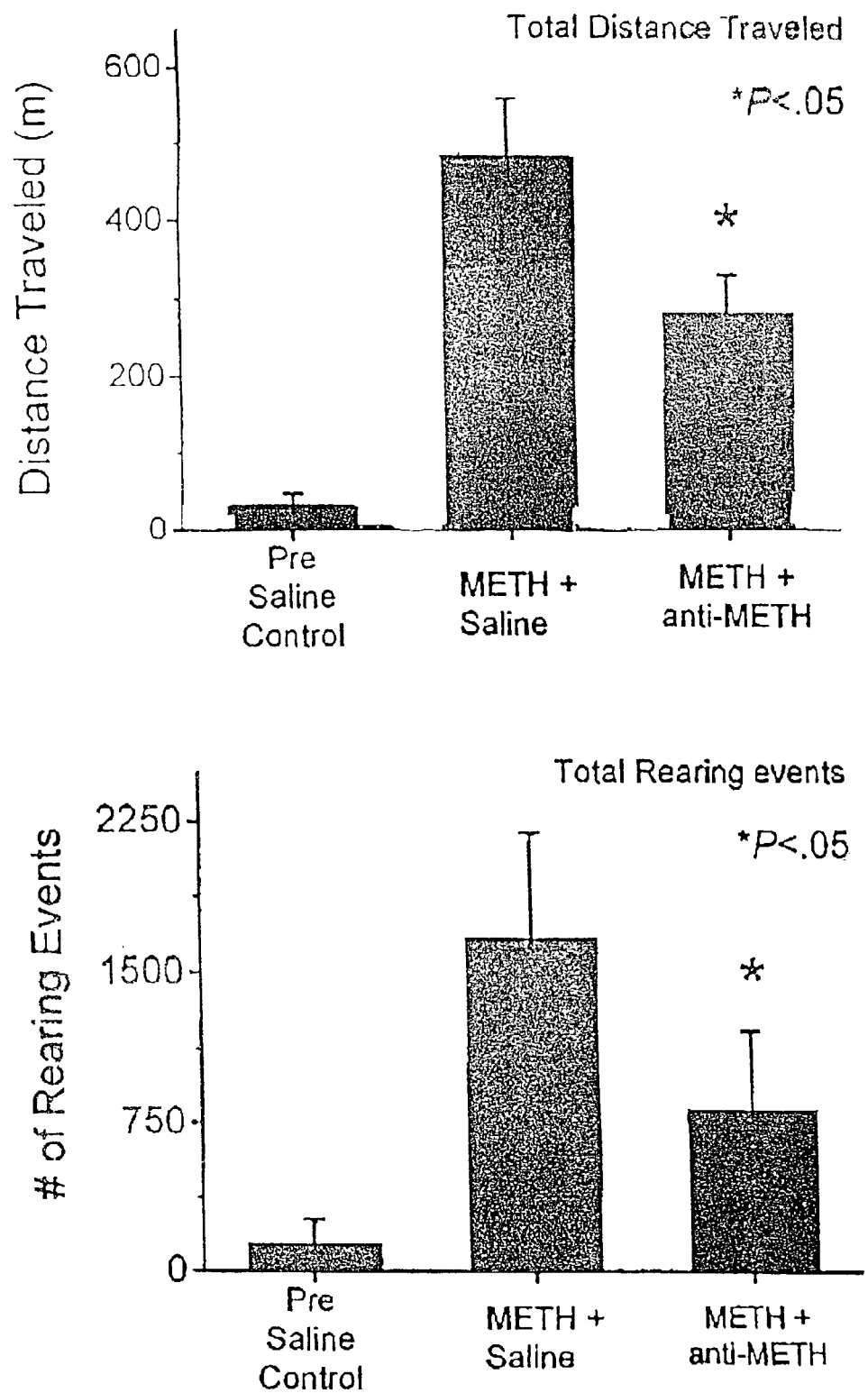
FIG. 16 shows the use of anti-(+)METH monoclonal antibodies as a pretreatment to reduce drug effects. (administered the day a 1 mg/kg methamphetamine challenge dose) the anti-(+) methamphetamine monoclonal antibody significantly ($P<0.05$) reduced (+)methamphetamine induced effects by 42% for distance traveled (left) and by 51% for rearing events (right).

Pretreatment with Anti-(+) Methamphetamine Monoclonal Antibody to Reduce the Effects Of (+)Methamphetamine Drug Abuse Rats (n=7/group) were administered a dose of 502 mg/kg of anti-methamphetamine monoclonal antibody on day 1. The following day they were administered i.v. (+)methamphetamine (1.0 mg/kg) 3 days apart on two occasions to stabilize locomotor responses and to minimize sensitization. Then 1.0 mg/kg of (+)methamphetamine was administered i.v. As shown in FIG. 16, the high-affinity anti-(+) methamphetamine monoclonal antibody significantly (P<0.05) reduced (+)methamphetamine induced effects by 42% for distance traveled (left) and by 51% for rearing events (right). The monoclonal antibody significantly shortened the duration of action of (+)methamphetamine from about 160 to 80 min. Saline control treatments conducted before and after the experimental protocol showed that baseline activity was stable over an extended period.

EXAMPLE 13

Impact of Anti-D-Methamphetamine Therapy on Drug Self-Administration and Drug Discrimination as a Measure of Treating Long-Term Addiction This example describes the ability of anti-d-methamphetamine antibody to alter the d-methamphetamine dose-response curve for the discriminative stimulus effects of d-methamphetamine, thereby demonstrating possible therapeutic usefulness of antibody treatment for methamphetamine abuse.

One of the problems in designing experiments to determine if antibody treatment affects drug discrimination is that antibodies have a very long duration of action (Proksch et al, 2000). For example, the half life of a monoclonal IgG in rats is about 8 days (Bazin-Redureau et al, 1997). If the same animals are used to determine the effects of drug doses before and after antibody treatment, the presence of the antibody might disrupt further drug-discrimination training through antibody binding of the training dose and reduced access of the training dose to the brain. Should this occur, maintenance of drug-discrimination control by (+)-methamphetamine might erode. Therefore, (+)-amphetamine and cocaine were used in addition to (+)-methamphetamine as training drugs in some experiments. These drugs do not cross react with (+)-methamphetamine-specific antibodies and either of these drugs can substitute for that drug as a discriminative stimulus. Thus the specificity of the anti-(+)-methamphetamine antibody should allow continued discrimination training using cocaine or (+)-amphetamine as the training drug.

In addition, the discriminative stimulus effects of (+)-methamphetamine, (+)-amphetamine, and cocaine were compared in rats and pigeons using several routes of drug administration. After determination of the dose-response curves for these drugs, anti (+)-methamphetamine antibodies were given intravenously and all or portions of the (+)-methamphetamine dose-response curves were redetermined. In pigeons, the dose-response curves for (+)-amphetamine and cocaine were determined before and after the administration of antibody to determine the in vivo specificity of an anti (+)-methamphetamine antibody in blocking the discriminative stimulus effect of (+)-methamphetamine. Dose-response curves for (+)-amphetamine were also determined after administration of this antibody to rats.

Experimental Protocols

A total of 16 adult male Sprague Dawley rats were employed. Three rats performed poorly during drug discrimination training and two others died before sufficient data were collected. Therefore, the rodent data presented are based on 11 rats, as shown in Table 3. All rats were maintained at body weights of approximately 300 g by food pellets earned during test sessions, and supplemental feeding after test sessions and on days when the rats were not tested.

A total of 8 male White Carneau pigeons were used in these experiments. Four of the pigeons had performed extensively in previous experiments on drug discrimination (Li and McMillan, 2001; McMillan et al., 2001b), including experiments in which the discrimination of amphetamines had been studied. These birds were maintained at 80–85% of their free-feeding weights (range 429–510 g). The second group of four birds also had performed in previous drug-discrimination experiments (McMillan et al, 2001a), although (+)-amphetamine was not used as a training drug in these experiments until the present experiments.

Water was freely available in the home cages of both rats and pigeons and the vivarium was temperature and humidity controlled with a light cycle from 0700 to 1900 and a dark cycle from 1900 to 0700. Training and testing of both species occurred between 0900 and 1200.

Rats were tested in two-lever operant chambers (Gerbrands Model 7400) enclosed in sound-attenuating chambers (Gerbrands Model 7200). Each chamber contained a house light on the chamber ceiling and stimulus lights over the two levers mounted on the front panel of the chamber. A pellet dispenser delivered 97 mg Noyes food pellets into a cup centered between the levers. Masking noise and air circulation were provided by a fan mounted in the rear wall of the sound-attenuating chamber. Programming and recording were accomplished by a MED Associates interface and microcomputer located in an adjacent room.

Testing Procedures

Rats were conditioned to lever press by autoshaping. After responding was established when lights above the right lever were lighted during one session, responses produced food pellets until 25 pellets had been delivered. In the next session a similar procedure was followed for the left lever. Subsequently, the lights above both levers were lighted and discrimination training began. Prior to training sessions, rats were administered a drug or 0.9% saline solution and placed in the operant chamber for 10 min after which the session began. The different training drugs, doses and routes of administration employed for the three groups of rats are shown in Table 3.

TABLE 3

Testing Of Rats And Pigeons Before And After mAb6H8 Administration

| GROUP | Training Drug and Dose | n | Testing Conditions |
|---|---|---|---|
| Rat I | 2 mg/kg (+) METH[a] | 4 | IV and IP (+) METH DRCs pre-antibody |
|  |  |  | IV (+) METH doses days 1 and 4 after antibody |
|  |  |  | IP (+) METH doses on days 1 and 4 after second antibody administration |
| Rat II | 5 mg/kg Cocaine | 3 | IV and IP (+) METH DRCs pre antibody |
|  |  |  | IV (+) METH 1 day after antibody |
|  |  |  | IP (+) METH days 1 and 7 after a second antibody administration |
| Rat III | 10 mg/kg Cocaine | 4 | Cumulative IP DRCs for Cocaine, (+) METH and (+) AMP |
|  |  |  | Cumulative IV DRCs for (+) METH |
| Pigeon I | 2 mg/kg (+) AMP | 4 | Cumulative IM DRCs for Cocaine, (+) METH, and (+) AMP |
|  |  |  | IM (+) METH DRCs day 1 and 8 post antibody |
| Pigeon II | 3 mg/kg (+) AMP | 4 | Cumulative IM DRCs for Cocaine, (+) METH and (+) AMP |
|  |  |  | IM (+) METH DRCs day 2 and 7 post antibody |

(+) METH = (+)-methamphetamine;
(+) AMP = (+)-amphetamine;
DRC = dose-response curve;
IV = intravenous drug adminstration;
IP = intraperitoneal drug administration;
IM = intramuscular drug administration.
One rat in group Rat I was trained with 1 mg/kg rather than 2 mg/kg (+)-methamphetamine.

Rats were tested until responding stabilized at more than 90% of responding on the drug key after the training drug and less than 10% of responding on the drug key after saline. After responding stabilized, dose-response curves were determined for all rats for (+)-methamphetamine by both the intravenous (IV) a n d intraperitoneal (IP) routes before administration of the antibody. For rats in Groups I and II, single points on the dose-response curve were determined on Tuesdays and Fridays with additional training occurring on other week days. For rats in Group III cumulative dose-response curves were determined on Fridays, with additional training on other week days. Testing did not occur on Saturday or Sunday.

On test days for Groups I and II, rats were given a dose of drug and then placed in the test cage for 10 min, after which the session began. The session terminated whenever the animal completed 20 responses on one of the two levers, or after 40 min, whichever occurred first. On test days for Group III, rats were treated similarly, except that after the first food pellet was consumed, the rats were removed from the test chamber and a second dose was given. The rats were then returned to the test chamber and 10 min later the session was reinitiated. This process of cumulative dosing continued until the animals no longer responded for a period of 10 min. The cumulative doses shown in the figures represent the sum of all doses given within the session.

The pigeons used in these experiments had performed in experiments previously. Those in pigeon Group I had been used most recently in an experiment where the birds were trained using 4 response keys to discriminate among saline, 5 mg/kg pentobarbital, 5 mg/kg morphine and 2 mg/kg (+)-amphetamine. In these experiments, responses on the correct key were reinforced under a fixed-ratio 20 schedule of food presentation (Li and McMillan, 2001). These birds continued to be trained and tested in this same chamber, except that training sessions with pentobarbital and morphine were discontinued, while those with 2 mg/kg (+)-methamphetamine and saline continued.

On training days, (+)-amphetamine or saline was injected into the breast muscle and the bird was placed in the test chamber for 10 min, after which the chamber and the response keys were illuminated and the session was initiated. Training continued for 40 min or until the pigeons had received 20 reinforcers, whichever occurred first. Once a week, a cumulative dose-response curve w as determined for cocaine, (+)-amphetamine, or (+)-methamphetamine. In the determination of cumulative dose-response curves, a dose of drug was administered and the pigeon was placed in the chamber for 10 min, after which the chamber and key lights were illuminated. The pigeon was tested for 5 min or until one food reinforcer had been delivered, whichever occurred first. Food was delivered following the completion of 20 responses on one of the two keys. After food had been delivered, or the session had timed out, the bird was removed from the chamber, a higher dose was administered, and the process was repeated. Cumulative dosing continued until the pigeon failed to respond during a 5-min period.

In other experiments with some of these pigeons, cumulative dose-response curves were determined for (+)-methamphetamine before, and at 1 and 8 days after, administration of the Ab6H8 antibody (pigeon Groups 1 and 2) or at 1 and 4 days after the administration of the mAb6H4 antibody (pigeon Group 2). Because only a few birds were still available for these experiments, the data for days 1–2 and days 7–8 were combined.

Drugs (+)-methamphetamine, (+)-amphetamine and cocaine were purchased from Sigma Chemical Co. as the hydrochloride salts. All doses are expressed as the salts. Drugs were dissolved in physiologic saline solution such that doses could be administered in a volume of 0.1 ml/100 g of body weight. Injections were given i.v. or i.p. to rats and intramuscularly to pigeons 10 min before test sessions. The anti (+)-methamphetamine antibody was administered at least one day before determining the discriminative stimulus effects of drugs.

Data Analysis

The percentage of responses on the drug key during training sessions were averaged across animals and a standard deviation was plotted around these means. Dose-response curves before and after administration of the antibodies were compared using a repeated measures analysis of variance.

Results

After responding stabilized, the baseline performance of the three groups of rats during training sessions was not significantly different, indicating that stimulus control was equivalent across the three groups. Although a two-way repeated measures. ANOVA for i.v. dose-response curves for (+)-methamphetamine in groups I and II was statistically significant, subsequent Tukeys tests revealed no additional significant differences between groups, nor were there statistically significant differences in dose-response curves across groups when drugs were administered by the i.p. route. Therefore, data from the rats trained with (+)-methamphetamine and cocaine were combined for the determination of dose-response effects to increase group size.

Figure 17:
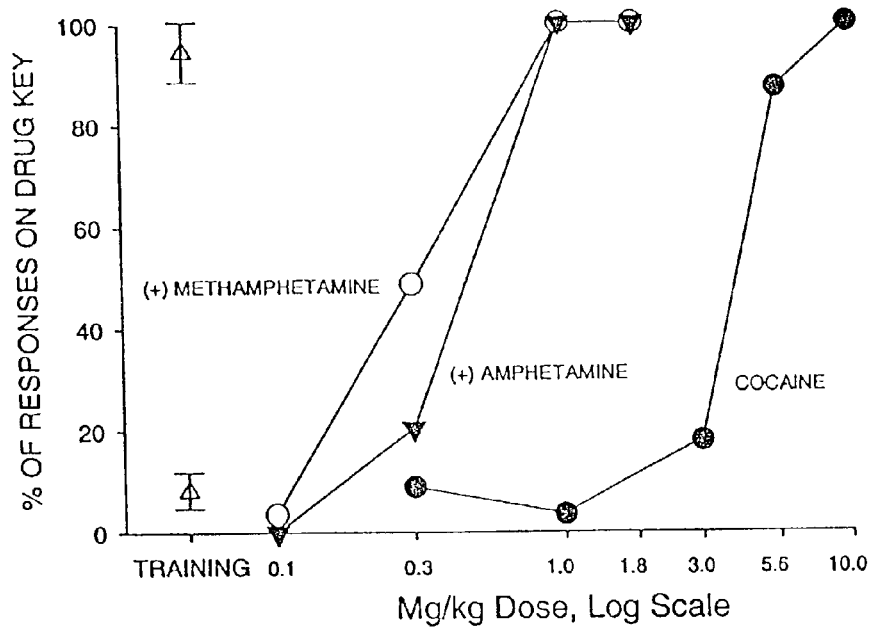
FIG. 17 shows cumulative i.p. dose-response curves for (+)-methamphetamine, (+)-amphetamine and cocaine in rats trained to discriminate 10 mg/kg cocaine from saline (Table 3, Rat Group III). Abscissa: Mg/kg dose on a log scale. Ordinate: Percentage of responses on the drug (cocaine) key. Each point on the (+)-methamphetamine and (+)-amphetamine dose-response curves represents single observations in the same four rats, while points on the cocaine dose-response curves represent duplicate observations in the same rats. Brackets at TRAINING show +/− one standard deviation around mean for six training sessions with saline and six training sessions with cocaine after responding stabilized.

FIG. 17 compares the discriminative stimulus effects of i.p. doses of (+)-methamphetamine, (+)-amphetamine and cocaine in the rats from group III. Low doses of all three drugs produced responding on the saline key, while higher doses of these drugs produced responding on the drug key. (+)-Methamphetamine and (+)-amphetamine were nearly equipotent as discriminative stimuli, but cocaine was only about one-tenth as potent as the amphetamines.

Figure 18:
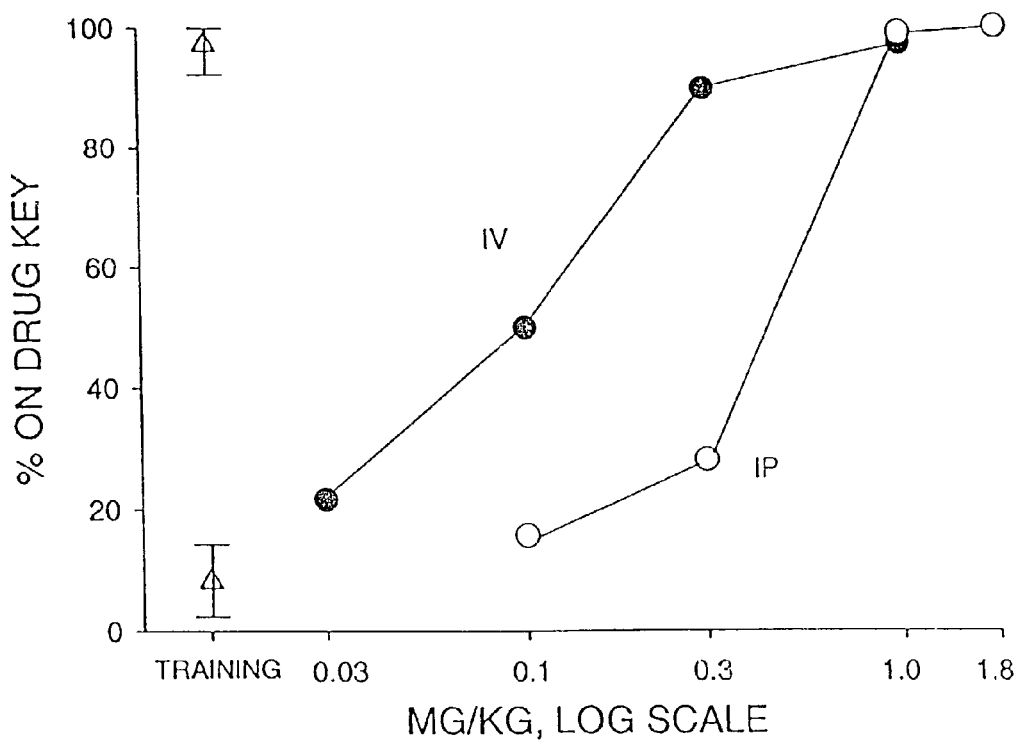
FIG. 18 shows cumulative dose-response curves for i.v. and i.p. (+)-methamphetamine in rats. Abscissa: Mg/kg (+)-methamphetamine on a log scale. Ordinate: Percentage of responses on the drug key. Each point represents single observations in each of eleven rats. The rats were trained to discriminate between saline and 10 mg/kg cocaine, or 5 mg/kg cocaine, or 1 or 3 mg/kg (+)-methamphetamine (see Table 3). Brackets at TRAINING represent six training sessions after saline and six training sessions after drug after responding stabilized.

FIG. 18 shows a comparison between the effects of i.v. and i.p. doses of (+)-methamphetamine conducted in all 11 rats. At low doses of (+)-methamphetamine responding was confined largely to the saline key. As the dose of (+)-methamphetamine increased, responding shifted to the drug key. Intravenous (+)-methamphetamine was approximately 3 times more potent than i.p. (+)-methamphetamine.

Figure 19:
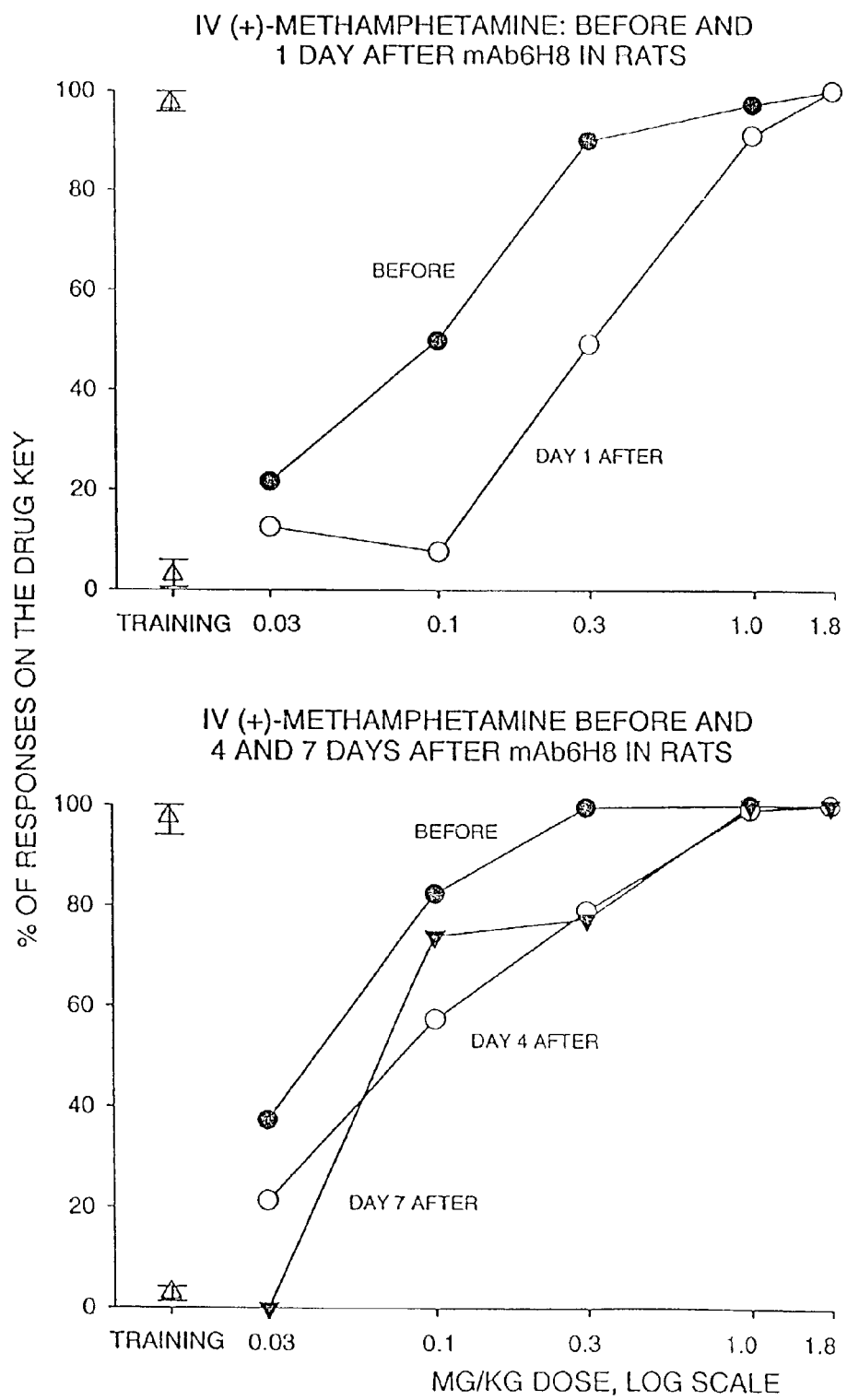
FIG. 19 shows dose-response curves for i.v. (+)-methamphetamine before and 1 day after treatment with 1 g/kg of the mAb6H8 antibody in rats (top panel) or before and 4 and 7 days after the antibody treatment (bottom panel). Abscissa: Mg/kg (+)-methamphetamine on a log scale. Ordinate: percentage of responses on the drug key. All 7 rats from Groups I and II (Table 3) contributed to the dose-response curves in the top panel, but only 5 of these rats contributed to the data in the bottom panel. Brackets at TRAINING represent six training sessions after saline and six training sessions after drug after responding stabilized.

The top frame of FIG. 19 shows the effects of i.v. (+)-methamphetamine before and 1 day after the administration of the low-affinity mAb6H8, and the bottom frame shows data from the same rats before and 4 and 7 days after administration of the mAb6H8. Administration of the antibody shifted the (+)-methamphetamine dose-response curve approximately 3-fold to the right (top frame) on the day after administration of the antibody. A one-way repeated measure ANOVA showed the dose response curves to be significantly different. The bottom frame of FIG. 19 shows the dose-response curves for i.v. (+)-methamphetamine at 4 and 7 days after administration of the antibody. Both dose-response curves after the antibody were significantly shifted to the right (p<0.05).

Figure 20:
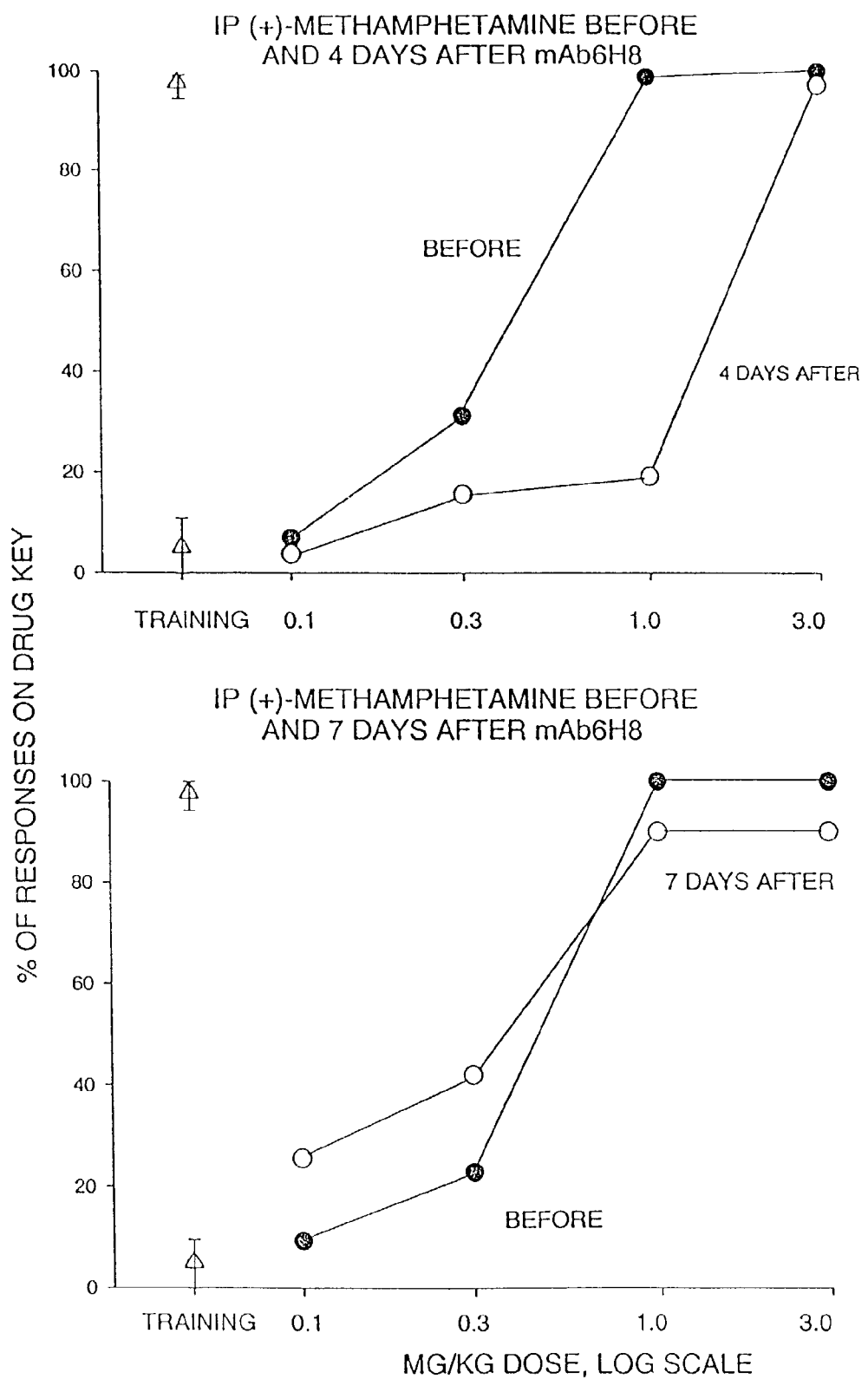
FIG. 20 shows dose-response curves for i.p. (+)-methamphetamine before and 4 days (top panel) or 7 days (bottom panel) after treatment with 1 g/kg of the mAb6H8 in rats. Abscissa: Mg/kg (+)-methamphetamine on a log scale. Ordinate: Percentage of responses on the drug key. All 7 rats from Groups I and II (Table 3) contributed to the data in the bottom panel, but only 5 of these rats contributed to the data in the top panel. Brackets at TRAINING represent six training sessions after saline and six training sessions after drug after responding stabilized.

FIG. 20 shows the i.p. (+)-methamphetamine dose-response curve before and 4 days (top frame) and 7 days (bottom frame) after administration of mAb6H8. At 4 days after administration of the antibody the (+)-methamphetamine dose-response curve was shifted approximately 3-fold to the right, a shift that was statistically significant (p=<0.05) by a repeated measures ANOVA. By day 7 there was no significant difference between the before and after dose response curves.

Figure 21:
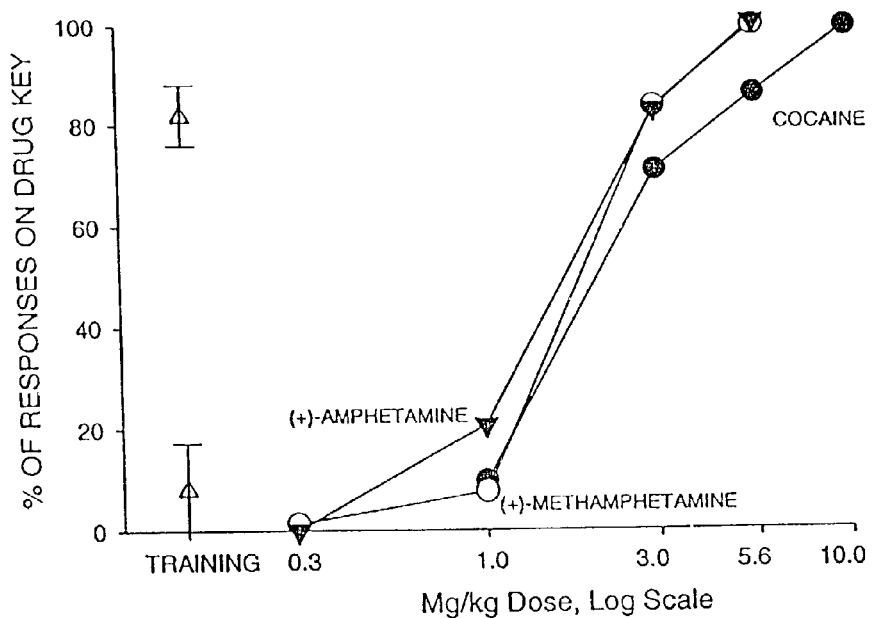
FIG. 21 shows cumulative i.m. dose-response curves for (+)-methamphetamine, (+)-amphetamine and cocaine in pigeons trained to discriminate 2 or 3 mg/kg (+)-amphetamine from saline. Abscissa: Mg/kg dose on a log scale. Ordinate: Percentage of responses on the drug [(+)-amphetamine] key. Each point on the dose-response curves represents duplicate observations in the pigeons in Group I and single observations in pigeons in Group II (Table 3), except at the highest dose of each drug where only 3 or 4 birds responded. Brackets at TRAINING show +/- one standard deviation around mean for six training sessions with saline and six training session with cocaine after responding stabilized.

FIG. 21 shows the effects of intramuscular injections of (+)-methamphetamine, (+)-amphetamine, and cocaine in pigeons trained to discriminate 2 or 3 mg/kg (+)-amphetamine from saline. Low doses of all drugs produced responding primarily on the saline key and higher doses produced responding on the drug key. (+)-Methamphetamine and (+)-amphetamine were approximately equipotent, while cocaine was about one-third as potent as the amphetamines.

Figure 22:
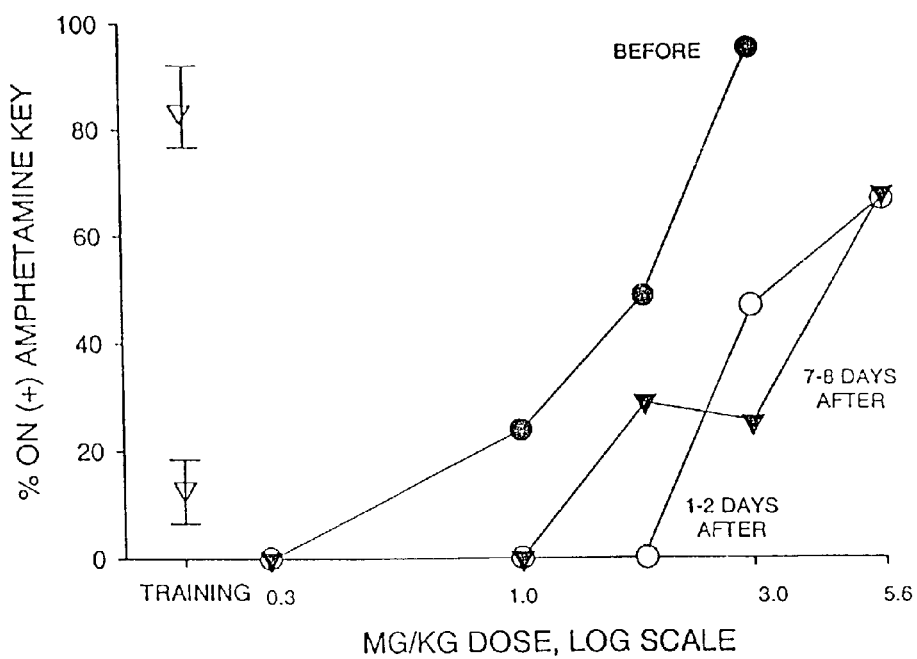
FIG. 22 shows dose-response curves for i.m. (+)-methamphetamine before and 1 and 2, or 7 and 8 days after treatment with 1 g/kg of mAb6H8 in pigeons. Abscissa: Mg/kg (+)-methamphetamine on a log scale. Ordinate: Percentage of responses on the drug key. Two pigeons from Pigeon Group 1 and four pigeons from Pigeon Group 2 contributed to these experiments. Brackets at TRAINING represent six training sessions after saline and six training sessions after drug after responding stabilized.

FIG. 22 shows the effects of intramuscular doses of methamphetamine in pigeons at 2 and 7 days after administration of mAb6H8. At 2 days after the antibody, the (+)-methamphetamine dose-response curve was shifted slightly downward and to the right relative to its original position. At 7 days after mAb6H8 the shift was 3–10 fold.

Figure 23:
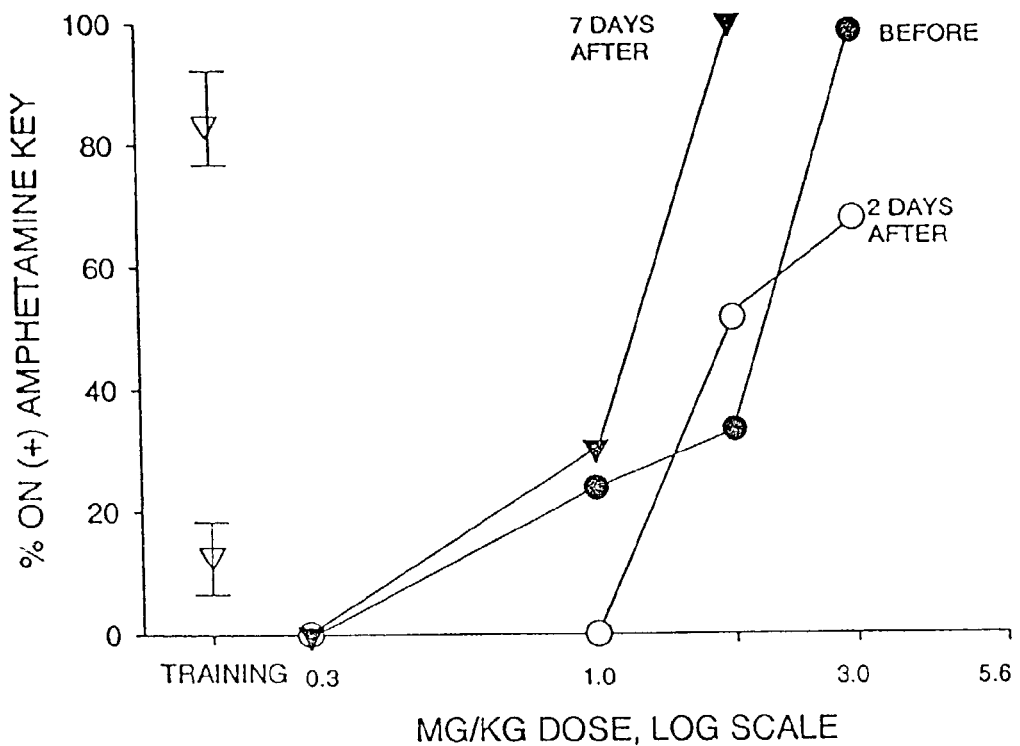
FIG. 23 shows dose-response curves for intramuscular (+)-amphetamine before and 2 or 7 days after treatment with 1 g/kg of mAb6H8 in pigeons. Abscissa: Mg/kg (+)-amphetamine on a log scale. Ordinate: Percentage of responses on the drug key. Two pigeons from Pigeon Group 1 and four pigeons from Pigeon Group 2 contributed to these experiments. Brackets at TRAINING represent six training sessions after saline and six training sessions after drug after responding stabilized.

FIG. 23 shows the effects of intramuscular (+)-amphetamine in pigeons at 2 and 7 days after mAb6H8. The dose-response curves at 2 and 7 days after mAb6H8 for (+)-amphetamine were not statistically different. The dose-response curve for responding on the drug key reached a peak at a lower dose of (+)-amphetamine 7 days after than it had before the antibody was given.

Figure 24:
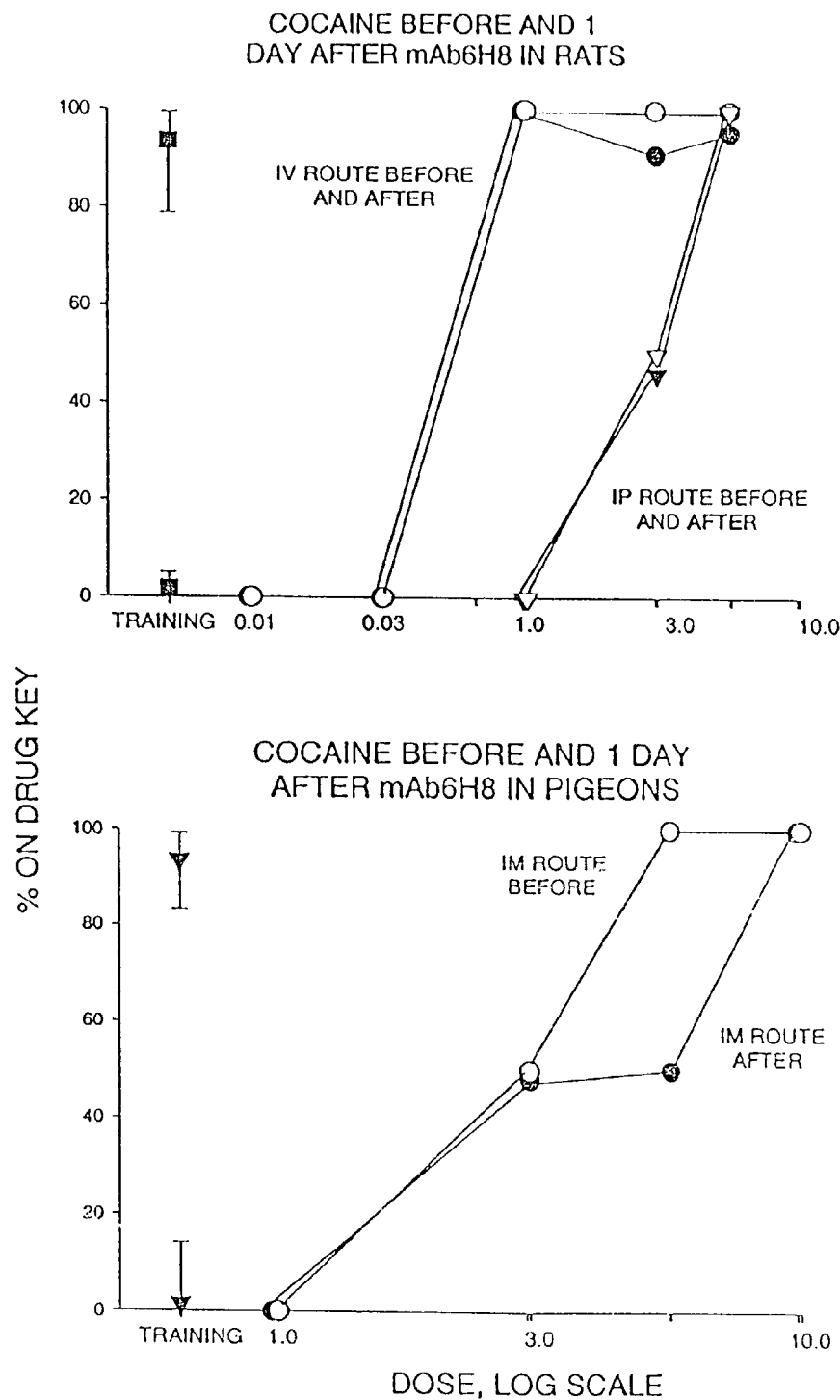
FIG. 24 shows dose-response curves for cocaine administered by i.v. and i.p. routes (rats, top panel) or i.m. route (pigeons, bottom panel) before and 1 day after administration of mAb6H8. Abscissa: Mg/kg cocaine on a log scale. Ordinate: Percentage of responses on the drug key. Each point on the dose-response curves represents single observations in two animals from the Rat III group or Pigeon II group. Brackets at TRAINING represent six training sessions after saline and six training sessions for these same subjects.

FIG. 24 shows the effects of i.v. and i.p. cocaine in rats before and 1 day after mAb6H8 (top frame) and the effects of i.m. cocaine in pigeons before and 1 day after the antibody (bottom frame). The cocaine curves were not shifted after administration of the antibody in either rats or pigeons.

Figure 25:
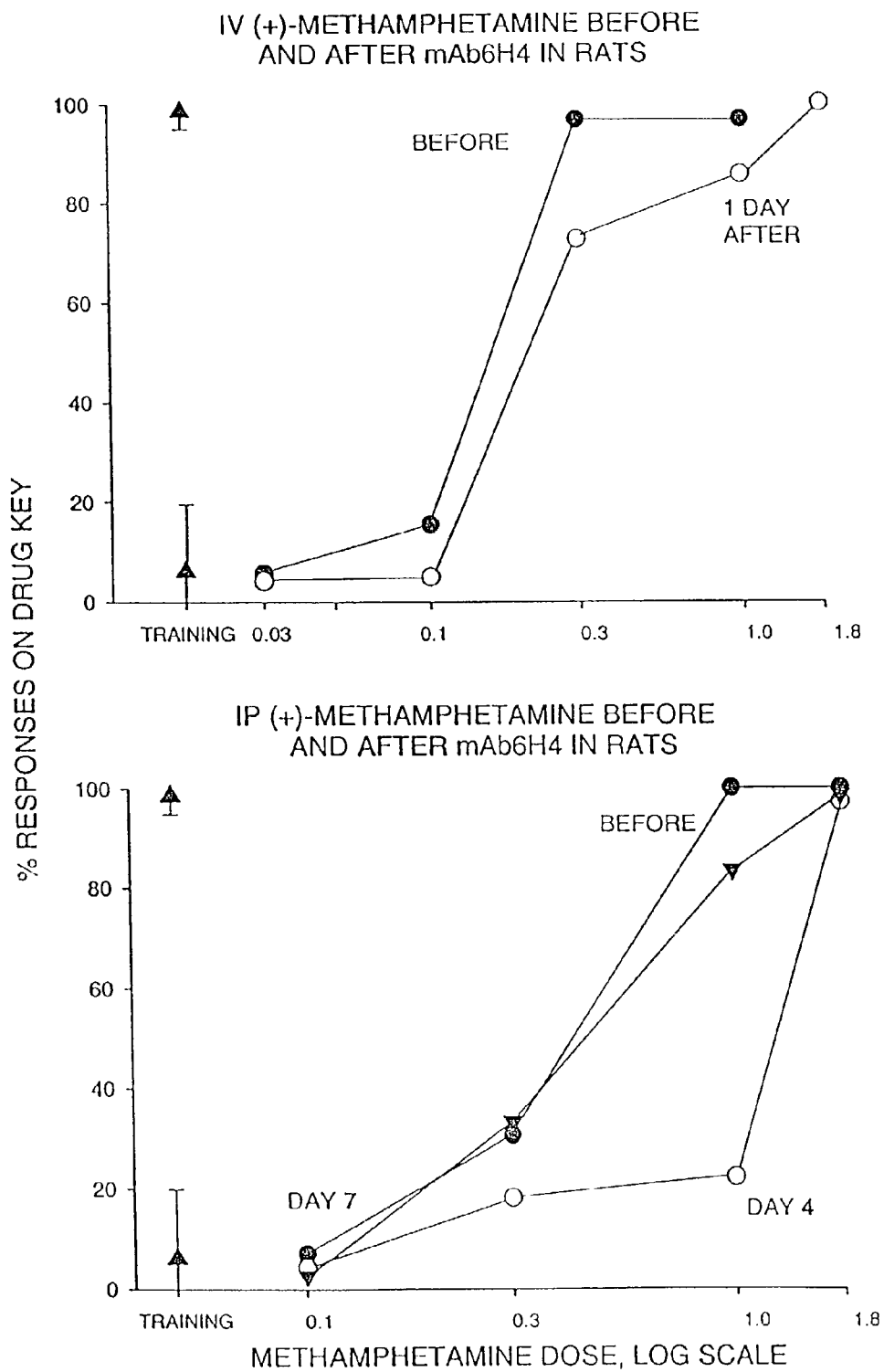
FIG. 25 shows dose-response curves for i.v. (+)-methamphetamine 1 day (top panel) or 4 and 7 days after the administration of mAb6H4 in rats. Abscissa: Mg/kg (+)-methamphetamine on a log scale. Ordinate: Percentage of responses on the drug key. Brackets at TRAINING show +/- one standard deviation around mean for six training sessions with saline and six training session with cocaine after responding stabilized.

FIG. 25 shows the effects of intravenous administration of (+)-methamphetamine to rats before and 1 day after (top frame) and at days 4 and 7 after the administration of the high-affinity mAb6H4 anti-methamphetamine antibody. The antibody shifted the (+)-methamphetamine dose-response curve slightly to the right 1 day after its adminstration. At day 4 the dose-response curve was shifted to the right by 3–10 fold. By day 10 after administration of the mAb6H4 the methamphetamine dose-response curve was close to its original position.

Figure 26:
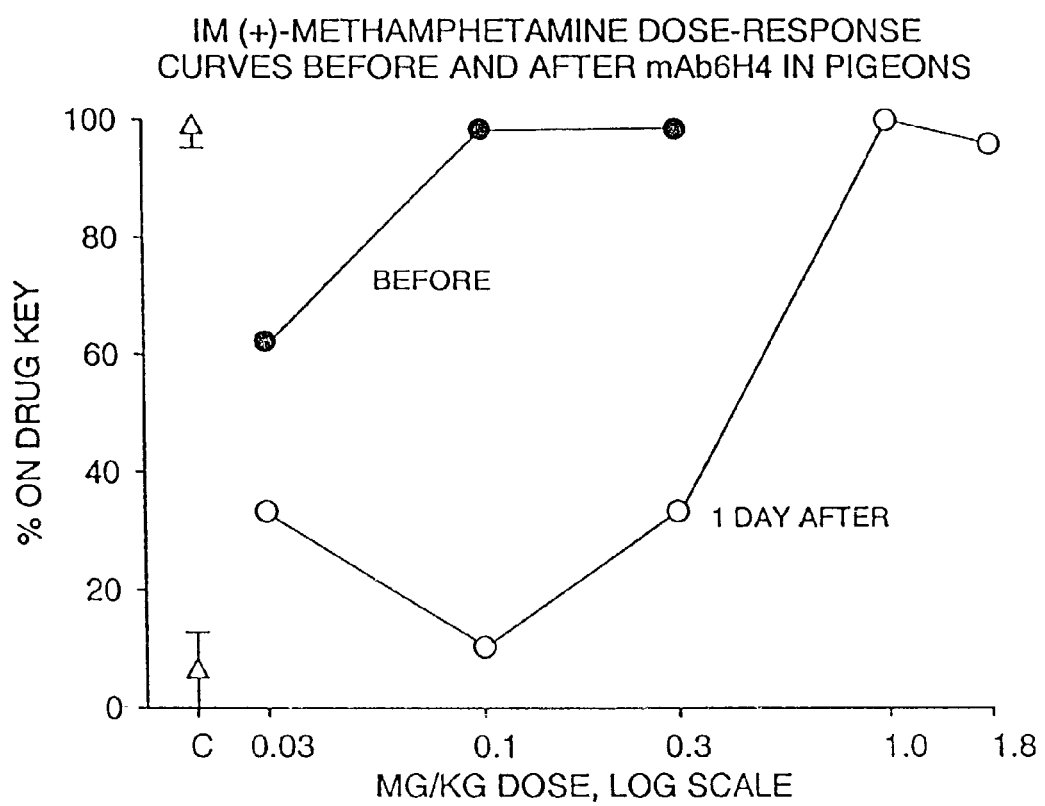
FIG. 26 shows dose-response curves for intramuscular (+)-methamphetamine before and 1 day after 1 g/kg of mAb6H4 in pigeons. Abscissa: Mg/kg (+)-methamphetamine on a log scale. Ordinate: Percentage of responses on the drug key. Three pigeons from Pigeon Group 2 contributed to these experiments. Brackets at TRAINING show +/- one standard deviation around mean for six training sessions with saline and six training session with (+)-amphetamine after responding stabilized.

FIG. 26 shows the i.m. dose-response curves for (+)-methamphetamine before and 1 day after administration of the high-affinity mAb6H4 in pigeons. The antibody shifted the dose response curve to the right by approximately 10-fold.

These results show that a low affinity ($K_D$=250 nM) anti-(+)-methamphetamine monoclonal antibody (mAb6H8) shifted the (+)-methamphetamine dose-response curve to the right by about one-half log unit. This effect was robust since it occurred in both rats and pigeons, it occurred after intravenous (rats), intraperitoneal, (rats) and intramuscular (pigeons) routes of (+)-methamphetamine administration, and it occurred when different training doses of (+)-methamphetamine, cocaine, and (+)-amphetamine were used during discrimination training. A similar shift was shown with the high affinity mAb6H4 antibody ($K_D$=10 nm).

Although only two rats and two pigeons were available to study the discriminative stimulus effects of (+)-amphetamine and cocaine before and after the administration of the mAb6H8 antibody, the failure of the anti (+)-methamphetamine antibody to shift the dose-response curves for the discrimination of either of these drugs given by several routes of administration suggests that its effects were specific for (+)-methamphetamine. The failure of the antibody to block the effects of cocaine were observed using two different routes of cocaine administration in rats (i.v. and i.p.) and by a third route in pigeons (i.m.). Therefore, despite the small number of animals used in these experiments, the generality of these findings was established. Although (+)-methamphetamine and (+)-amphetamine differ little in chemical structure and in their potency as discriminative stimuli, mAb6H8 has an approximate 2,000 times lower affinity for (+)-amphetamine, so the failure of the antibody to shift the (+)-amphetamine dose-response curve was not unexpected.

Preliminary data suggest that (+)-methamphetamine and (+)-amphetamine are nearly equipotent as discriminative stimuli in the rat. This represents a potential problem because in rats a considerable fraction of (+)-methamphetamine is metabolized to (+)-amphetamine. In fact, in the rat peak plasma levels of (+)-amphetamine are obtained within 20 min after intravenous administration of (+)-methamphetamine (Rivière et al., 1999; 2000). Conversion of (+)-methamphetamine to (+)-amphetamine in rats might explain why the shift in the (+)-methamphetamine dose-response curve was only modest in rats. It is possible that much of the (+)-methamphetamine not bound to the antibody was metabolized to (+)-amphetamine. Since the discriminative stimulus properties of (+)-methamphetamine and (+)-amphetamine are difficult to separate, the formation of (+)-amphetamine might have limited the degree to which mAb6H8 could shift the (+)-methamphetamine dose-response curve in rats. In pigeons, the anti (+)-methamphetamine antibody also shifted the (+)-methamphetamine dose-response curve about one-half log unit to the right. The metabolism of (+)-methamphetamine in pigeons is not known.

The effects of mAb6H8 lasted for a week or longer in both rats and pigeons. The half life of mAb6H8 is not known; however, previous studies with anti-phencyclidine IgG antibodies have shown a functional elimination half-life of 15.4 days, which produced significant reductions in brain phencyclidine for at least 27 days (Proksch et al., 2000). The behavioral data suggest an extended functional half-life for the anti-(+)-methamphetamine antibody, but not as long as the anti-phencyclidine MAb.

In these experiments, (+)-methamphetamine, cocaine, and (+)-amphetamine were used as training drugs, and some times at different doses. Differences in dose-response curves for these drugs that were dependent on the training drug or the training dose were not observed. The fact that the dose-response curve for (+)-methamphetamine in the presence of mAb6H8 consistently shifted to the right by approximately one-half log unit despite the differences in the training drug and training dose only strengthens the generality of the findings.

In the present experiments (+)-methamphetamine and (+)-amphetamine were found to be equipotent as discriminative stimuli in rats trained to discriminate 10 mg/kg cocaine from saline. Both the amphetamines were approximately 10 times more potent than cocaine (FIG. 17). These data are similar to previous reports on the relative potency of cocaine and the amphetamines a s discriminative stimuli in rats. In previous studies in cocaine-trained rats, (+)-methamphetamine and (+)-amphetamine have ranged from 3–30 times more potent than cocaine as a discrimininatve stimulus. In (+)-methamphetamine trained rats, methamphetamine was 10 times more potent than cocaine. In pigeons in the present study, (+)-methamphetamine and (+)-amphetamine also were approximately equipotent, but the amphetamines were only 2–3 times more potent than cocaine. This is similar to a previous report in pigeons trained to discriminate cocaine from saline, where little difference was found between the potency of cocaine and (+)-amphetamine. Although the present study found less difference in potency between the amphetamines and cocaine, it is possible that this difference relates to differences in the training drugs rather than the species in the present study. The rats in which the dose-response curves were determined were trained to discriminate 10 mg/kg cocaine from saline, while the pigeons in which the dose-response curves were determined were trained to discriminate 3 mg/kg (+)-amphetamine from saline.

The potency of intravenous and intraperitoneal (+)-methamphetamine was also compared in rats. These experiments were performed because preliminary experiments with the anti (+)-methamphetamine antibody suggested that it was more difficult to shift the (+)-methamphetamine dose-response in the presence of the antibody when the (+)-methamphetamine was administered intravenously instead of intraperitoneally. When more animals were tested, this observation did not hold up. However, it was established that intravenous (+)-methamphetamine was approximately 3 times more potent as a discriminative stimulus than intraperitoneal (+)-methamphetamine in rats trained to discriminate cocaine from saline.

The degree to which the 6H8 anti-(+)-methamphetamine shifted the drug discrimination curve for (+)-methamphetamine was modest. Presumably, the effectiveness of the antibody would be related to its affinity (250 nM), capacity, and the on-off rates of mAb binding to (+)-methamphetamine. The mAb6H8 antibody is a low affinity antibody. Antibodies with significant improvements in the affinity constant and specificity should be more effective than mAb6H8. The high affinity mAb6H4 did appear to produce a greater shift in the dose-response curve for (+)-methamphetamine in pigeons than mAb6H8 did. The research with both mAb6H8 and mAb6H4 illustrates that anti-(+)-methamphetamine monoclonal antibodies are capable of blocking pharmacological effects of (+)-methamphetamine that are relevant to its abuse.

EXAMPLE 14

Effect of Antibody-Based Therapy on D-Methamphetamine Toxicity in Large Animal Model A battery of pharmacokinetics studies and behavioral tests can be conducted to determine whether anti-d-methamphetamine Fab can reverse acute behavioral toxicity due to d-methamphetamine in large animals like large dogs or primates. These data will help to determine the ability of anti-d-methamphetamine Fab to redistribute d-methamphetamine in a large animal model and help to scale-up the therapy to humans. d-Methamphetamine can be administered to male dogs (or primates; n=6 per group, 3 males and 3 females) at 0.3 mg/kg or higher depending on results of preliminary d-methamphetamine dose-response studies. If needed for quantitation, a tracer dose of [$^3$H]-d-methamphetamine can also be administered. After the drug is fully distributed (e.g., 30–45 min), anti-d-methamphetamine Fab is administered at a 1.0 mol-eq dose to the amount of d-methamphetamine remaining in the dog (or primate) at 30 min. The exact timing and dosing depend on the outcome of the rat studies an d preliminary pharmacokinetic studies in dogs or primates. Plasma and urine d-methamphetamine pharmacokinetics can be determined in each dog or primate as described above.

The same dogs (or primates) should be used for the pharmacokinetic and behavioral studies for continuity. However, the success of the experiments is not dependent on using the same dog (or primate) for all experiments (n=6). For the behavioral experiments, d-methamphetamine are administered to dogs (or primates) at 0.3 mg/kg (or higher) followed 30–45 min later by a 0.1, 0.3, or 1.0 mol-eq dose of anti-d-methamphetamine Fab. The experiments are done in a pre-determined repeated-measures, mixed-sequence design. The same measures of behavior (and the EthoVision system) as described above can be used in the studies of d-methamphetamine acute toxicity.

The following references were cited herein:

Bazin-Redureau et al., *J Pharm Pharmacol* 49:277–281 (1997).
Byrnes-Blake et al., *Int Immunopharmacol* 1:329–338 (2001).
Cho et al., *Synapse* 39:161–166 (2001).
Collings, *Cable News Network* Feb. 13 (1996).
Cook et al., *Drug Metab Dispos* 21:717–723 (1993).
Davis and Preston, *Anal Biochem* 116:402–407 (1981).
Goding, Monoclonal Antibodies: Principles and Practice, p.118–122, Academic Press, New York (1983).
Hardin et al., *J Pharmacol Exp Ther* 285:1113–1122 (1998).
Khor et al., *Drug Metab Dispos* 19:486–490 (1991).
Laurenzana et al., *Drug Metab. Dispos.* 23:271–278 (1995).
Li and McMillan, *Behav Pharmacol* 12:621–628 (2001).
McMillan et al., *Behav Pharmacol* 12:195–208 (2001a).
McMillan et al., *Pharmacol Biochem Behav* 68:395–402 (2001b).
Minh-Tam et al., *Anal. Biochem.* 116:402–407 (1981).
Owens et al., *J. Pharmacol. Exp. Ther.* 246:472–478 (1988).
Proksch et al., *J Pharmacol Exp Ther* 292:831–837 (2000).
Rowland and Tozer, *Clinical Pharmacokinetics: Concepts and Applications,* 3rd ed, Williams & Wilkins, Baltimore (1995).
Rivière et al., *J Pharmacol Exp Ther* 291:1220–1226 (1999).
Rivière et al., *J Pharmacol Exp Ther* 292:1042–1047 (2000).
Tempest et al., *Biotechnology* 9:266–271, (1991).
Triplett et al., *J Pharm Sci* 74:1007–1009 (1985).
Valentine et al., *J Pharmacol Exp Ther* 278:709–716 (1996).
Valentine and Owens, *J. Pharmacol. Exp. Ther.* 278:717–724 (1996).

Any patents or publications mentioned in this specification are indicative of the levels of those skilled in the art to which the invention pertains. These patents and publications are herein incorporated by reference to the same extent as if each individual publication was specifically incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A monoclonal antibody or an antigen binding fragment thereof that specifically recognizes d-methamphetamine, d-amphetamine, (+/−) 3,4-methylenedioxymethamphetamine or (+/−) 3,4-methylenedioxyamphetamine, wherein said monoclonal antibody or the antigen binding fragment thereof is generated using an immunogen comprising a substituted d-methamphetamine as a hapten and an immunogenic carrier, wherein said substituted d-methamphetamine has a structure

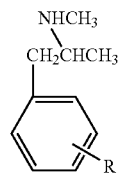

wherein R is substituted on the aromatic ring at one of C2, C3 or C4;
wherein R is —ZR$_2$COOR$_1$;
Z is O or S;
R$_1$ is H or R$_4$;
R$_2$ is a C$_{2-9}$ alkyl chain containing an O or a N(R$_3$) moiety therein, a C$_{2-9}$ alkenyl chain or a C$_{2-9}$ alkynyl chain;
R$_3$ is C$_{1-5}$ alkyl; and R$_4$ is —CH$_2$CH$_2$CN, 4-nitrophenyl, 2,3,4,5,6-pentafluorophenyl; or 2,3,5-trichlorophenyl; or a hydrochloride salt thereof.

2. The monoclonal antibody of claim 1, wherein said antibody is monoclonal antibody 6H8 or wherein said antibody is monoclonal antibody 6H4.

3. The monoclonal antibody of claim 1, wherein R is OCH$_2$CH=CH(CH$_2$)$_x$COOH, and x is 1 to 6.

4. The monoclonal antibody of claim 1, wherein R is OCH$_2$C=C(CH$_2$)$_x$COOH, and x is 1 to 6.

5. The monoclonal antibody of claim 1, wherein R is O(CH$_2$)$_x$O(CH$_2$)$_y$COOH, and x is 2 to 4, y is 1 to 5.

6. The monoclonal antibody of claim 1, wherein R is O(CH$_2$)$_x$NR$_3$(CH2)$_y$COOH, x is 2 to 3 and y is 1 to 5.

7. The monoclonal antibody of claim 1, wherein R is SCH$_2$CH=CH(CH$_2$)$_x$COOH, and x is 1 to 6.

8. The monoclonal antibody of claim 1, wherein R is SCH$_2$C=C(CH$_2$)$_x$COOH, and x is from 1 to 6.

9. The monoclonal antibody of claim 1, wherein R is S(CH$_2$)$_x$O(CH$_2$)$_y$COOH, and x is 2 to 4, y is 1 to 5.

10. The monoclonal antibody of claim 1, wherein R is S(CH$_2$)$_x$NR$_3$(CH$_2$)$_y$COOH, x is 2 to 3 and y is from 1 to 5.

* * * * *